US009110062B2

(12) United States Patent
Gurbel

(10) Patent No.: US 9,110,062 B2
(45) Date of Patent: Aug. 18, 2015

(54) ASSESSMENT OF CARDIAC HEALTH AND THROMBOTIC RISK IN A PATIENT

(71) Applicant: Paul A. Gurbel, Baltimore, MD (US)

(72) Inventor: Paul A. Gurbel, Baltimore, MD (US)

(73) Assignee: Paul A. Gurbel, Baltimore, MD (US)

( * ) Notice: Subject to any disclaimer, the term of this patent is extended or adjusted under 35 U.S.C. 154(b) by 0 days.

(21) Appl. No.: 13/860,424

(22) Filed: Apr. 10, 2013

(65) Prior Publication Data

US 2014/0100167 A1    Apr. 10, 2014

Related U.S. Application Data

(63) Continuation of application No. 13/290,377, filed on Nov. 7, 2011, now Pat. No. 8,440,420, which is a continuation of application No. 12/099,727, filed on Apr. 8, 2008, now Pat. No. 8,058,023, which is a continuation of application No. 11/070,845, filed on Mar. 1, 2005, now Pat. No. 7,381,536.

(51) Int. Cl.
G01N 33/53      (2006.01)
G01N 33/569     (2006.01)
C12Q 1/56       (2006.01)
G01N 33/86      (2006.01)

(52) U.S. Cl.
CPC ............ *G01N 33/56966* (2013.01); *C12Q 1/56* (2013.01); *G01N 33/86* (2013.01)

(58) Field of Classification Search
CPC ........................................................ C12Q 1/56
USPC ........................................... 435/13, 214, 217
See application file for complete search history.

(56) References Cited

U.S. PATENT DOCUMENTS

| 6,797,519 B2 | 9/2004 | Cohen et al. |
| 7,381,536 B2 | 6/2008 | Gurbel |
| 8,058,023 B2 | 11/2011 | Gurbel |
| 8,440,420 B2 | 5/2013 | Gurbel |

OTHER PUBLICATIONS

Ajzenberg, et al. (2005) "Enhanced Shear-Induced Platelet Aggregation in Patients Who Experience Subacute Stent Thrombosis", *Journal of the American College of Cardiology*, vol. 45, No. 11;1753-56.
Barragan et al. "Resistance to Thienopyridines: Clinical Detection of Coronary Stent Thrombosis by Monitoring of Vasodilator-Stimulated Phosphoprotein Phosphorylation" *Catheter Cardiovasc Interv.* 2003;59:295.
Cuisset, et al. "High Post-Treatmetn Platelet Reactivity Identified Low-Responders to Dual Antiplatelet Therapy at Increased Risk of Recurrent Cardiovascular Events After Stenting for Acute Coronary Syndrome", *Journal of Thrombosis and Haemostasis*, 2006 4: 542-549.
Elwood, P., et al. "Ischemic Heart Disease and Platelet Aggregation: The Caerphilly Collaborative Heart Disease Study", *Circulation*. 1991, vol. 83, No. 1, pp. 38-44.
Fateh-Moghadam, et al. "Changes in Surface Expression of Platelet Membrane Glycoproteins and Progression of Heart Transplant Vasculopathy", *Circulation*. 2000 102:890-897.
Frossard, et al. "Platelet Function Predicts Myocardial Damage in Patients with Acute Myocardial Infarction", *Circulation*. 2004; 110:1392-1397.
Grotemeyer, "The Platelet-Reactivity-Test—A Useful "By-Product" of the Blood-Sampling Procedure?", Thrombosis Research, 61:423-431 (1991).
Grotemeyer, et al. (1993) "Two-year follow-up of aspirin responder and aspirin non responder. A pilot-study including 180 post-stroke patient" *Throm Res* 7(5):397-403.
Gum et al. "A Prospective, Blinded Determination of the Natural History of Aspirin Resistance Among Stable Patients with Cardiovascular Disease", *J Am Coll Cardiol*. 2003;4:961.
Gurbel et al. "A New Method of Representing Drug-Induced Platelet Inhibition: Better Description of Time Course, Response Variablity, Non-Response, and Heightened Reactivity", *Platelets*. 2003;14:481.
Gurbel, et al. "Effects of reteplase and alteplase on platelet aggregation and major receptor expression during the first 24 hours of acute myocardial infarction treatment. GUSTO-III Investigators. Global Use of Strategies to Open Occluded Coronary Arteries" *J. Am. Coll. Cardiol*. 1998; 31:1466-1473.
Gurbel "Clopidogrel Response Variablity and Drug Resistance", Haematologica. 2004; 89; Supplement 7;9-11.
Gurbel et al. "Failure of Clopidogrel to Reduce Platelet Reactivity and Activation Following Standard Dosing in Elective Stenting: Implications for Thrombotic Events and Restenosis", Platelets. 2004; 15(2):95-99.
Gurbel et al. "Interpretation of Platelet Inhibition by Clopidogrel and the Effect of Non-Responders" J Thromb Haemost. 2003;1:1318-1320.
Gurbel et al. "Platelet Activation in Myocardial Ischemic Syndromes", *Expert Rev Cardiovasc Ther*. 2004; 2(4):89-99.
Gurbel et al. "The Stratification of Platelet Reactivity and Activation in Patients with Stable Coronary Artery Disease on Aspirin Therapy" *Thromb Res* 2003; 112:9-12.
Gurbel et al. "Clopidogrel Effect on Platelet Reactivity in Patients with Stent Thrombosis", *Journal of the American College of Cardiology*, 2005, vol. 46, No. 10, pp. 1827-1832.
Gurbel et al. "Clopidogrel for Coronary Stenting Response Variability, Drug Resistance, and the Effect of Pretreatment Platelet Reactivity", *Circulation*. 2003;107:2908.

(Continued)

*Primary Examiner* — Bin Shen
(74) *Attorney, Agent, or Firm* — Carol L. Francis; Bozicevic, Field & Francis LLP

(57) ABSTRACT

The invention features methods and compositions for assessing risk, particularly immediate risk, of thrombotic events in patients with suspected or known vascular disease, and more particularly to assessing risk of thrombotic events in patients with coronary artery disease, particularly acute myocardial infarction, stroke, unstable angina, stable angina, or restenosis. Risk of thrombosis can be assessed by analysis of platelet reactivity and/or velocity of thrombin or fibrin formation, and determining whether the patient has a score associated above a risk threshold value. In other embodiments, risk of thrombosis in a patient is evaluated in the context of a profile generated from values obtained from one or more assays that evaluate various factors associated with thrombosis and/or atherosclerosis.

25 Claims, 20 Drawing Sheets

(56) References Cited

OTHER PUBLICATIONS

Gurbel et al. "Clopidogrel Loading with Eptifibatide to Arrest the Reactivity of Platelets—Results of the Clopidogrel Loading with Eptifibatide to Arrest the Reactivity of Platelets (Clear Platelets) Study", *Circulation*. 2005;111:1153-1159.

Gurbel et al. "Clopidogrel: The Future Choice for Preventing Platelet Activation During Coronary Stenting?" *Pharm Res* 1999; 65: 109.

Hampton, J., et al. "Platelets and Coronary Disease, Round Three", *British Medical Journal*. 1985, vol. 290, pp. 414-415.

Kabbani et al. "Platelet Reactivity Characterized Prospectively", *Circulation*. 2001; 104:181.

Kabbani et al. "Usefullness of Platelet Reactivity Before Percutaneous Coronary Intevention in Determining Cardiac Risk One Year Later", *Am J Cardiol*. 2003; 91:876.

Lam, J., et al. "Platelet Aggregation, Coronary Artery Disease Progression and Future Coronary Events", *The American Journal of Cardiology*. 1994, vol. 73, pp. 333-338.

Lanza, et al. "Relation Between Platelet Response to Exercise and Coronary Angiographic Findings in Patients with Effort Angina", *Circulation*. 2003;107:1378-1382.

Lennon et al., "A Comparison of Plateletworks™ and Platelet Aggregometry for the Assessment of Aspirin-Related Platelet Dysfunction in Cardiac Surgical Patients", Journal of Cardiothoracic and Vascular Anesthesia, 18(2):136-140 (2004).

Lev, et al., "Aspirin and Clopidogrel Drug Response in Patients Undergoing Percutaneous Coronary Intervention", *J Am Coll Cardiol.*, 2006, vol. 47, No. 1, pp. 27-33.

Lordkipanidzé et al., "Evaluation of the platelet count drop method for assessment of platelet function in comparison with "gold standard" light transmission aggregometry", Thrombosis Research, 124:418-422 (2009).

Matetzky et al. "Clopidogrel Resistance Is Associated with Increased Risk of Recurrent Atherothrombotic Events in Patients with Acute Myocardial Infarction", *Circulation*. 2004;109:3171-3175.

McGill et al. "Abnormal Platelet Reactivity in Men with Premature Coronary Heart Disease", *Coronary Artery Disease*. 1994. 5:889-900.

Meade, T., et al. "Epidemiological Characteristics of Platelet Aggregability", *British Medical Journal*. 1985, vol. 290, pp. 428-432.

Mobley et al. "Frequency of Nonresponse Antiplatelet Activity of Clopidogrel During Pretreatment for Cardiac Catheterization", *Am J Cardiol*. 2004;93:456.

Muller et al. "Prevalence of Clopidogrel Non-Responders Among Patients with Stable Angina Pectoris Scheduled for Elective Coronary Stent Placement", *Thromb Haemost*. 2003;89:783-7.

Muller et al. "Effect of a High Loading Dose of Clopidogrel on Platelet Function in Patients Undergoing Coronary Stent Placement" Heart: Science Letter 2001; 85:92-93.

Prisco & Paniccia (2003) "Point-of-Care Testing of Hemostasis in Cardiac Surgery" *Thrombosis Journal* 1:1-10.

Regar et al. "Incidence of Thrombotic Stent Occlusion During the First Three Months After Sirolimus-Eluting Stent Implantation in 500 Consecutive Patients", *Am J Cardiol*. 2004;93:1271.

Ruggeri "Platelets in Atherothrombosis", *Nature Medicine*, 2002, vol. 8, No. 11, pp. 1227-1234.

Samara et al. "The Difference Between Clopidogrel Responsiveness and Posttreatment Platelet Reactivity", *Thromb Haemostat*. 2005 115:89-94.

Tantry et al. "What is the Best Measure of Thrombotic Risks—Pretreatment Platelet Aggregation, Clopidogrel, Responsiveness, or Posttreatment Platelet Appregation?" *Catheterization and Cardiovascular Interventions*, 2005, 66:597-598.

Thaulow, et al., "Blood Platelet Count and Function are Related to Total and Cardiovascular in Apparently Healthy Men", *Circulation*, 1991, 84:613-617.

Trip, et al. "Platelet Hyperreactivity and Prognosis in Survivors of Myocardial Infaction", *The New England Journal of Medicine*, 1990, vol. 322, No. 22, pp. 1549-1554.

Tschoepe, et al. "Platelet Membrane Activation Markers Are Predictive for Increased Risk of Acute Ischemic Events After PTCA", *Circulation*, 1993, vol. 88, No. 1, pp. 37-42.

Van Werkum et al., "A comparison between the Plateletworks™-assay and light transmittance aggregometry for monitoring the inhibitory effects of clopidogrel", Intl J Cardiol., 140:123-126 (2008).

Van Werkum et al., "Point-of-care platelet function testing in patients undergoing PCI: between a rock and a hard place", Netherlands Heart Journal, 15(9):299-305 (2007).

Wilhelmsen, L., at al. "Thrombocytes and Coronary Heart Disease", *Circulation*. 1991, vol. 84, No. 2, pp. 936-938.

Wu & Hoak, "A New Method for the Quantitative Detection of Platelet Aggregates in Patients with Arterial Insufficiency" The Lancet, 2:924-927 (1974).

Yee et al. "Aggregometry Detects Platelet Hyperreactivity in Healthy Individuals" *Blood*, 2005, vol. 106, No. 8, pp. 2723-2729.

Zimmermann et al. "Functional and Biochemical Evaluation of Platelet Aspirin Resistance after Coronary Artery Bypass Surgery" *Circulation*. 2003;108:542.

Post-Treatment Aggregation (5 µM ADP) in patients without Stent Thrombosis (NO SAT) and With Stent Thrombosis (SAT)

Figure 2 Post-Treatment Aggregation (20 μM ADP) in patients without Stent Thrombosis (NO SAT) and With Stent Thrombosis (SAT)

Thromboelastography MA Analysis in patients without Stent Thrombosis (NO SAT) and
With Stent Thrombosis (SAT)

ASSESSMENT OF CARDIAC HEALTH AND THROMBOTIC RISK IN A PATIENT

This application is a continuation of U.S. application Ser. No. 13/290,377, filed Nov. 7, 2011, now U.S. Pat. No. 8,440,420, which application is a continuation of U.S. application Ser. No. 12/099,727, filed Apr. 8, 2008, now U.S. Pat. No. 8,058,023, which application is a continuation of U.S. application Ser. No. 11/070,845, filed Mar. 1, 2005, now U.S. Pat. No. 7,381,536,

FIELD OF THE INVENTION

The present invention relates generally to assessing risk of a thrombotic event and associated cardiac events, including assessing risk of ischemic and bleeding events, particularly acute myocardial infarction, in patients with suspected or known vascular disease.

BACKGROUND OF THE INVENTION

Preventative care and selection of therapy for patients with suspected or known vascular disease remains a difficult task for clinicians. There are no currently available methods that completely assess the immediate risk of developing myocardial ischemia or infarction from thrombosis or atherosclerosis. Importantly, there are significant limitations of the methods now used to assess the acute risk of thrombosis or bleeding in patients with suspected or known vascular disease, particularly where the patient is receiving anti-thrombotic therapy. In addition, percutaneous intervention can increase the risk of a thrombotic event and therapies used to decrease this risk can cause bleeding.

At present, available indicators are only indirect methods for assessing such risks, since they do not reflect the risk of the final event in vessel occlusion and thrombosis. Indirect measurements include:
1. Cholesterol level: High cholesterol levels are associated with the formation of atherosclerotic plaque formation;
2. LDL cholesterol level: This "bad" type of cholesterol, with high levels associated with accelerated atherosclerotic plaque formation;
3. LDL cholesterol particle size: Particle size is another measurement of the "bad" type of cholesterol, often signifying a genetic predisposition towards the development of atherosclerosis. Small LDL particles can be seen in various hyperlipidemic states and the metabolic syndrome;
4. HDL cholesterol level: This "good" type of cholesterol, with high levels being a positive predictor in controlling the development of atherosclerosis;
5. HDL cholesterol particle size: Particle size is another measurement of this "good" type of cholesterol with large particles conferring the most protection against atherosclerosis;
6. Triglyceride level: High levels are associated with various hyperlipidemic states and the metabolic syndrome which predispose patients to atherosclerosis;
7. Glucose measurements: Glucose intolerance and diabetes mellitus are associated with accelerated atherosclerosis (coronary heart disease and peripheral vascular disease). Glucose levels can be measured by standard assays. The hemoglobin A1C (glycosylated hemoglobin) is a measure of overall glycemic control. The glucose tolerance test indicates a patient's ability to clear glucose from the circulation following a glucose challenge;
8. Homocysteine levels: High levels are associated with accelerated atherosclerotic plaque formation;
9. Inflammatory markers: High levels of markers such as, e.g., C-reactive protein, Interleukin-6, and myeloperoxidase, are associated with acute myocardial infarction and the development of atherosclerosis;
10. Assessment of coagulation status: Coagulation status, as assessed by, for example, prothrombin time (PT), International Normalized Ratio (INR) and partial thromboplastin time (PTT) are insufficient measures of thrombosis risk and are used to gauge anti-coagulation status (blood-thinning);

Assessing risk of a thrombotic event is of particular importance to medical treatment of all patients where coagulation is concerned. For instance, when a patient with vascular disease is about to undergo or has undergone percutaneous intervention to relieve an arterial or vascular stenosis. Such interventions include angioplasty and stenting. Such patients are routinely treated with a variety of thrombosis inhibitors (e.g., anti-platelet drugs) to reduce the risk of acute vessel occlusion. However, at the same time, such inhibitors increase the risk of bleeding. Despite the risks, such thrombosis inhibitors are generally administered in the same dose to all patients. Since there are no universally accepted methods to assess the risk of thrombosis and acute myocardial infarction in a patient, clinicians choose instead to treat the patient with a standard dose of drugs in hopes of avoiding an event having an unknown risk. As a result, it is likely that many patients are unnecessarily over-treated with drug(s) that are associated with dangerous, life-threatening side effects. Alternatively, some patients do not achieve adequate protection against thrombosis.

There is a need in the field for improved or alternative methods for assessing risk of thrombosis and immediate risk of a cardiac event in a patient, as well as methods for tailoring therapy based on this risk and/or the responsiveness of a patient to therapy. The present invention addresses these needs.

LITERATURE

Matetzky et al. Circulation. 2004; 109:3171-5; Kabbani et al. Am J. Cardiol. 2003; 91:876-8; Kabbani et al. Circulation. 2001; 104:181-6.
Samara et al. Thromb Haemostat. 2005 115:89-94; Muller et al. Thromb Haemost. 2003; 89:783-7; Gurbel et al. Circulation. 2003; 107:2908-13.
Gurbel et al. Pharm Res 1999; 65: 109-23; Gurbel et al. Platelets. 2004; 15:95-9; Gurbel et al. Thromb Res 2003; 112:9-12; Barragan et al. Catheter Cardiovasc Interv. 2003; 59:295-302; Gum et al. J Am Coll Cardiol. 2003; 4:961-5; Regar et al. Am J Cardiol. 2004; 93:1271-5; Gurbel et al. Haematologica. 2004; 89; Supplement 7; 9-11; Zimmermann et al. Circulation. 2003; 108:542-7; Mobley et al. Am J Cardiol. 2004; 93:456-8; Muller et al. Heart. 2001; 85:92-3; Gurbel et al. Platelets. 2003; 14:481-3; Gurbel et al. J Thromb Haemost. 2003; 1:1319-21; Gurbel et al. Expert Rev Cardiovasc Ther. 2004; 2:535-45

SUMMARY OF THE INVENTION

The invention features methods and compositions for assessing risk, particularly the immediate risk, of a thrombotic event in a patient, including myocardial ischemia from thrombotic and bleeding events, acute myocardial infarction, stroke, unstable angina, stable angina, or restenosis. Assessment in a patient with suspected or known vascular disease is of particular interest.

In an embodiment of particular interest, risk of a thrombotic event (e.g., immediate risk) is assessed by determining whether platelet reactivity score in a patient (e.g., by assessing platelet aggregation and other indicators associated with increased platelet reactivity) that is above a risk threshold value. In another embodiment of particular interest, risk of a thrombotic event (e.g., immediate risk) is assessed by determining whether a velocity of thrombin or fibrin formation score (e.g., by assessing time-to-thrombin formation or time-to-fibrin formation) is above a risk threshold value. In other embodiments, cardiac health, including the risk of a thrombotic event, in a patient is evaluated in the context of a profile generated from values obtained from one or more assays that evaluate various factors associated with, for example, thrombosis and/or atherosclerosis.

In one aspect the invention features a method of assessing risk of a thrombotic event in a patient by assessing platelet reactivity, time-to-thrombin formation (TTF), or time-to-fibrin formation (TFF) in a blood sample of a patient having or suspected of having vascular disease, said assessing providing a test score, wherein a test score greater than a risk threshold score indicates the patient is at risk of a thrombotic event.

In a related embodiment, the thrombotic event is a thrombosis, particularly a stent thrombosis. In further related embodiments, platelet reactivity is assessed independent of a pre-treatment baseline of platelet reactivity in the patient. In specific related embodiments, 1) platelet reactivity is assessed by 5 µM ADP-induced platelet aggregation and the risk threshold score is from about 24% to 36%; 2) platelet reactivity is assessed by 20 µM ADP-induced platelet aggregation and the risk threshold score is from about 40% to 60%; 3) platelet reactivity is assessed by a $P2Y_{12}$ reactivity ratio and the risk threshold score is from about 32 to about 48; and/or 4) platelet reactivity is assessed by stimulated GP IIb/IIIa expression and the risk threshold score is from about 32 to about 48. In one embodiment, platelet reactivity is assessed by a method other than thromboelastography maximum amplitude (MA).

In another embodiment, the methods are used to assess whether the risk of a thrombotic event is an immediate risk of a thrombotic event. In related embodiments, the immediate risk of a thrombotic event is risk of a thrombotic event within about 18 months, or within about 6 months. In further related embodiments, thrombotic event is a recurrent thrombotic event, such as myocardial ischemia.

In a related embodiment immediate risk of a thrombotic event is assessed by assessing at least one of platelet reactivity, time-to-thrombin formation (TTF) or time-to-fibrin formation (TFF), and further where 1) platelet reactivity is assessed by thromboelastography Maximum Amplitude (MA), the risk threshold score is from about 58 to 86; 2) platelet reactivity is assessed by 5 µM ADP-induced platelet aggregation, the risk threshold score is from about 45% to 55%; 3) platelet reactivity is assessed by 20 µM ADP-induced platelet aggregation, the risk threshold score is from about 52% to 76%; 4) where when TTF and TFF are assessed by thromboelastography R and the risk threshold score is from about 4.6 min to 5.6 min.

In further related embodiments, the thrombotic event is myocardial ischemia, myocardial infarction, unstable angina, stable angina, restenosis, stroke or deep vein thrombosis. In further embodiments, risk is assessed prior to percutaneous intervention or pharmacological intervention and/or in a patient undergoing therapy, e.g., with an anti-platelet inhibitor.

In still other embodiments, the methods further include modifying therapy to modulate a risk factor for a thrombotic event, e.g., to reduce platelet reactivity, or to increase at least one of TTF and TFF, in the patient.

In another aspect the invention features methods of assessing cardiac health in a patient by assessing at least one of platelet reactivity, time-to-thrombin formation (TTF), or time-to-fibrin formation (TFF) in a blood sample of a patient in a blood sample of a patient, said assessing providing a test score, where comparison of the test score to a risk threshold score is indicative of cardiac health in the patient.

In a related embodiment, platelet reactivity is assessed, and 1) where platelet reactivity is assessed by 5 µM ADP-induced platelet aggregation, a risk threshold score of from about 24% to 36% is indicative of risk of a thrombotic event in the patient; 2) where platelet reactivity is assessed by 20 µM ADP-induced platelet aggregation, a risk threshold score of from about 40% to 60% is indicative of a thrombotic event in the patient; 3) where platelet reactivity is assessed by a $P2Y_{12}$ reactivity ratio, a risk threshold score of from about 32 to about 48 is indicative of risk of a thrombotic event in the patient; or 4) where platelet reactivity is assessed by stimulated GP IIb/IIIa expression, a risk threshold score of from about 32 to about 48 is indicative of risk of a thrombotic event in the patient.

In further related embodiments, platelet reactivity is assessed, and further 1) where platelet reactivity is assessed by thromboelastography Maximum Amplitude (MA), a risk threshold score of from about 58 to 86 is indicative of immediate risk of a thrombotic event in the patient; 2) where platelet reactivity is assessed by 5 µM ADP-induced platelet aggregation, a risk threshold score of from about 45% to 55% is indicative of immediate risk of a thrombotic event in the patient; and/or 3) where platelet reactivity is assessed by 20 µM ADP-induced platelet aggregation, a risk threshold score of from about 52% to 76% is indicative of immediate risk of a thrombotic event in the patient.

In another related embodiment, at least one of TTF or TFF is assessed. Where TTF and TFF are assessed by thromboelastography R, a risk threshold score of from about 4.6 min to 5.6 min is indicative of immediate risk of a thrombotic event in the patient.

In still other related embodiments, the method of assessing cardiac health involves assessing one or more of a thrombotic event risk factor selected from a lipid risk factor, an inflammation risk factor, a oxidation marker, or a metabolic risk factor. The lipid risk factor is total cholesterol level, LDL cholesterol level, LDL cholesterol particle size, HDL cholesterol level, HDL cholesterol particle size, triglyceride level, LPa, or Lp-PLA2; the inflammation risk factor is a level of C-reactive protein, a level of IL-6, or a level of ICAM-1; the oxidation marker is a level of myeloperoxidase, a level of oxidized LDL, or a level of an oxidized fatty acid; and the metabolic risk factor is fasting glucose, a level of hemoglobin A1C, or a homocysteine level.

In another aspect the invention features methods of assessing risk of stent thrombosis in a patient, the method comprising assessing platelet reactivity in a blood sample of a patient having or suspected of having vascular disease, where said assessing provides a platelet reactivity test score, wherein a platelet reactivity test score greater than a risk threshold score indicates the patient is at risk of stent thrombosis. In related embodiments, platelet reactivity is assessed independent of a pre-treatment baseline of platelet reactivity in the patient.

In one embodiment, platelet reactivity is assessed 1) by 5 µM ADP-induced platelet aggregation, and the risk threshold score is from about 24% to 36%; 2) by 20 µM ADP-induced platelet aggregation, and the risk threshold score is from about 40% to 60%; 3) by $P2Y_{12}$ reactivity ratio, and the risk threshold score is from about 32 to about 48; and/or 4) by a level f stimulated GP IIb/IIIa expression, the risk threshold score is from about 32 to about 48. Preferably platelet reactivity is assessed by a method other than thromboelastography maximum amplitude (MA). In further related embodiments, assessment is performed is prior to percutaneous intervention or pharmacological intervention, and/or in a patient is undergoing therapy with an anti-platelet inhibitor (e.g., an ADP-induced platelet aggregation inhibitor). In further embodiment, the method further includes modifying therapy to reduce platelet aggregation in the patient.

In another aspect the invention features a method of assessing immediate risk of a thrombotic event in a patient, the method comprising assessing platelet reactivity, time-to-thrombin formation (TTF), or time-to-fibrin formation (TFF) in a blood sample of a patient having or suspected of having vascular disease, said assessing providing a test score; where comparison of the test score greater to a immediate risk threshold value is indicative of immediate risk of myocardial ischemia in the patient.

In a related embodiment, platelet reactivity is assessed, and 1) when platelet reactivity is assessed by thromboelastography Maximum Amplitude (MA), the risk threshold score is from about 58 to 86; 2) when platelet reactivity is assessed by 5 µM ADP-induced platelet aggregation, the risk threshold score is from about 45% to 55%; and 3) when platelet reactivity is assessed by 20 µM ADP-induced platelet aggregation and the risk threshold score is from about 52% to 76%. In a further related embodiment, at least one of TTF or TFF is assessed, and further where when TTF and TFF are assessed by thromboelastography R and the risk threshold score is from about 4.6 min to 5.6 min.

In another aspect, the invention features a method of treating a vascular disease in a patient, the method comprising administering a treatment regimen comprising administration of a active agent to a patient having vascular disease in an amount effective to decrease risk of a thrombotic event, wherein risk of the thrombotic event is assessed according to the methods described above and herein.

In another aspect the invention features a method of treating a vascular disease in a patient, the method comprising administering a treatment regimen comprising administration of a active agent to a patient having vascular disease; assessing a risk of a thrombotic event in the patient according to the methods described above and herein; and adjusting the treatment regimen so as to decrease the risk of a thrombotic event in the patient.

The invention is advantageous in that, prior to the present invention, no readily available or accepted methodology was available to directly assess risk of patients for a thrombotic event, including myocardial ischemia or myocardial infarction. Platelets play a fundamental role in the final event of vessel occlusion. Assessment of platelet reactivity predicts which patients are at higher risk for complications. Thus the invention provides the means to assess a patient's risk of different thrombotic events such as heart attack, stroke, and deep venous thrombosis. In the peri-operative state for surgeries (vascular, orthopedic and abdominal surgeries), the invention can identify which patients are predisposed to acute thrombotic events. The type of thrombotic event, for which the patient is at risk can readily be determined by the context in which the patient presents (e.g., in the context of other signs and symptoms associated with diagnosis of the underlying condition or disease).

The invention provides the advantage that platelet aggregation provides a marker for risk of a thrombotic event independent of responsiveness to drug therapy (e.g., as assessed by a change in platelet reactivity following administration of an anti-platelet drug such as clopidogrel, often referred to "drug responsiveness", e.g., "clopidogrel responsiveness"). For example, the inventor has found that clopidogrel resistance may overestimate the risk of stent thrombosis in non-responders with low pre-treatment platelet aggregation, and underestimate the risk of stent thrombosis in responders with high post-treatment platelet aggregation. Further, there is no need to assess platelet reactivity relative to a baseline of reactivity prior to administration of a therapy. Instead, a "raw" platelet reactivity score can be used to assess risk of for example, stent thrombosis or myocardial ischemia (such as myocardial infarction), and thus there is no need for a comparative analysis (e.g., between a pre-treatment score and a post-treatment score). As such the invention provides a method for assessing risk of a thrombotic event relative to a baseline of platelet reactivity, time-to-thrombin formation (TTF), or time-to-fibrin formation (TFF) that may have been present prior to drug-based therapy or other therapy.

The invention thus provides methods for assessing risk of a thrombotic event based on intrinsic platelet reactivity, TTF or RFF values independent of the baseline, and regardless of the presence or absence of the effect of any drugs or other therapy upon these characteristics.

The invention also provides methods and compositions that provide for coordination of results of various tests for risk factors associated with a thrombotic event (e.g., myocardial ischemia, atherosclerosis).

These and other advantages will be apparent to the ordinarily skilled artisan upon reviewing the present specification.

DEFINITIONS

Figure 1:
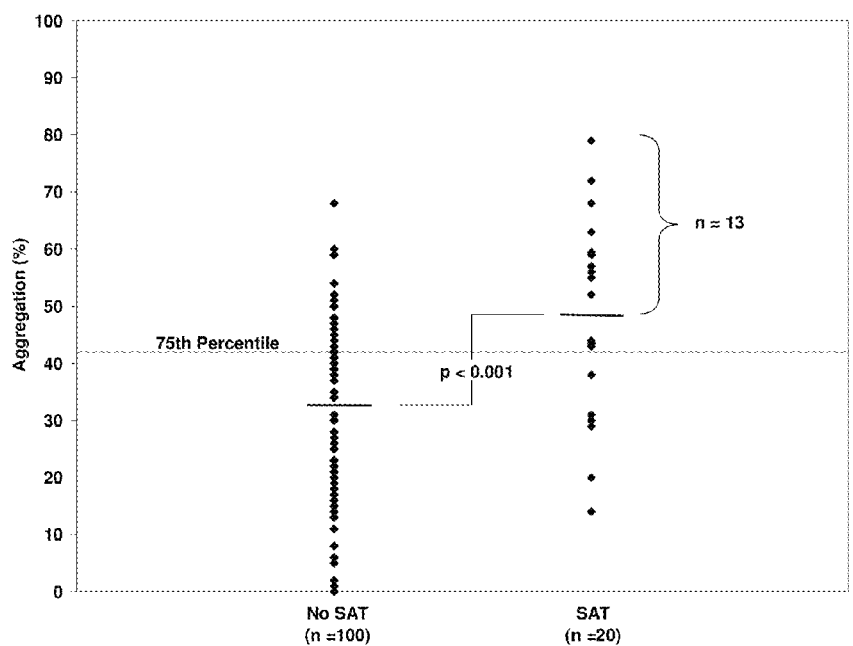
FIG. 1 is a graph showing ADP-induced platelet aggregation (5 µM) in patients with stent thrombosis (SAT) and without stent thrombosis (No SAT).

A "threshold score" or "risk threshold score" is a value for an assay for biological assay, e.g., platelet reactivity, time-to-thrombin formation (TTF), or time-to-fibrin formation (TFF), which is an approximate level, point, or value which distinguishes a relatively high risk of an event from a relatively low risk of an event. For example, in the context of platelet reactivity, in most cases the threshold score is an approximate value above which risk of a thrombotic event is relatively higher and below which risk of a thrombotic event is relatively lower. In the context of TTF and TFF, in most cases the threshold score is an approximate value below which risk of a thrombotic event is relatively higher and above which risk of a thrombotic event is relatively lower.

As used herein "borderline" refers to a platelet reactivity score that is about 10% above or below a risk threshold value, and "abnormal" is greater than or at a risk threshold value. Where a value above a risk threshold value indicates an increased risk (or immediate risk) of a thrombotic event, a patient can "borderline abnormal" if above the risk threshold value, but at less than or about 10% above the risk threshold value; likewise, a patient can be "borderline normal" if below the risk threshold value, but at less than or about 10% below the threshold. Similarly, where a value below a risk threshold value indicates an increased risk (or immediate risk) of a thrombotic event, a patient can "borderline abnormal" if below the threshold value, but at less than or about 10% below the risk threshold value; likewise, a patient can be "borderline normal" if above the platelet reactivity risk threshold value, but at less than or about 10% above the threshold.

A "platelet reactivity score" as used herein is meant to refer to a value obtained from assessment of platelet reactivity in a patient, where platelet reactivity is assessed by, for example conventional light transmittance aggregometry (for example, ADP-induced platelet aggregation) (e.g., 5 µM or 20 µM ADP) or thromboelastography.

A "time-to-thrombin formation (TTF) score" or "time-to-fibrin formation (TFF) score" is meant to refer to a value (usually expressed in minutes or seconds) obtained from assessment of TTF or TFF (e.g., by thromboelastography).

A "thrombotic event' is meant to include events associated with an arterial or vascular thrombus such as myocardial ischemia, heart attack (myocardial infarction, including acute myocardial infarction), stroke, cardiovascular death, angina (e.g., unstable angina), stent thrombosis, (including thrombosis associated with percutaneous intervention (e.g., stent thrombosis, stent re-stenosis) or other surgeries (e.g., vascular, orthopedic, or abdominal surgeries), deep venous thrombosis, stent re-stenosis, pulmonary embolus, and the like, particularly those which can lead to serious morbidity and/or mortality.

"Myocardial ischemia" as used herein refers to a low oxygen state due to obstruction of the arterial blood supply or inadequate blood flow leading to hypoxia in myocardial tissue. Thrombosis and atherosclerosis are two causes of myocardial ischemia referred to herein.

"Thrombosis" as used herein refers to the presence of a thrombus, an aggregation of blood factors, primarily platelets and fibrin with entrapment of cellular elements, which causes vascular obstruction at the point of formation.

"Atherosclerosis" as used herein refers to the progressive narrowing and hardening of the arteries over time so as to obstruct blood flow. This process generally occurs to some degree with age, but is accelerated with risk factors such as high cholesterol, high blood pressure, smoking, diabetes, and family history for atherosclerotic disease.

"Stenosis" as used herein refers to a narrowing of a vessel with arterial stenosis or vascular stenosis being of particular relevance to the present invention.

"Restenosis" as used herein refers to recurrence of stenosis after corrective surgery to remove or reduce a previous narrowing of an artery. Restenosis occurs most commonly after percutaneous intervention to treat atherosclerotic narrowings secondary to plaque buildup and thrombosis in arteries.

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "body fluid" and "bodily fluid," used interchangeably herein, refer to a biological sample of liquid from a mammal, e.g., from a human. Such fluids include aqueous fluids such as serum, plasma, lymph fluid, synovial fluid, follicular fluid, seminal fluid, amniotic fluid, milk, whole blood, urine, cerebrospinal fluid, saliva, sputum, tears, perspiration, mucus, tissue culture medium, tissue extracts, and cellular extracts. Particular bodily fluids that are interest in the context of the present invention include whole blood, serum, plasma, and other blood-derived samples, wherein the term "blood sample" is meant to encompass all such samples, with appropriate types of samples being selected according to any assay to be conducted.

A "computer-based system" refers to the hardware means, software means, and data storage means used to analyze information. The minimum hardware of a patient computer-based system comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" or "computing means" references any hardware and/or software combination that will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

By "clinical assay" is meant an assay or test that is performed on a sample obtained from an individual or patient (also referred to herein as host or patient) in order to provide information on current or future health or condition, diagnosis, treatment, prevention, and/or monitoring of a condition of the individual or patient.

The terms "evaluate" and "assess" are used interchangeably herein broadly to refer not only to the diagnosis or detection of a given condition of interest, but also to the monitoring of a condition over a given period of time. As such, in certain embodiments one uses the patient methods to assess the efficacy of a given treatment regimen for a given condition (e.g., a thrombotic or atherosclerotic condition.). In yet other embodiments, one uses the patient methods to monitor, predict, or track (i.e., watch or observe), the progression of a condition in a patient over a period of time.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and can include: (a) preventing the disease or a symptom of a disease from occurring in a patient which may be predisposed to the disease but has not yet been diagnosed as having it (e.g., including diseases that may be associated with or caused by a primary disease); (b) inhibiting the disease or condition, i.e., arresting its development; and (c) relieving the disease, i.e., causing regression of the disease.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, patient to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a sample" includes a plurality of such samples and reference to "the drug" includes reference to one or drugs and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention is based on the discovery that platelet reactivity, and more particularly platelet aggregation is a marker of the risk and occurrence of thrombotic events, including myocardial ischemic events in a patient having or suspected of having vascular disease, particularly in patients who have undergone percutaneous intervention and may be at acute risk of, for example, stent thrombosis, vessel restenosis, myocardial infarction and stroke. Importantly, platelet reactivity (e.g., as assessed by platelet reactivity), time to thrombin generation (also referred to herein as time-to-thrombin formation (TTF)), and time-to-fibrin generation (also referred to herein as time-to-fibrin formation (TFF)), are effective markers for risk of a thrombotic event, such as myocardial ischemia, independent of responsiveness to drug therapy (e.g., as assessed by a change in platelet reactivity following administration of an anti-platelet drug such as clopidogrel, often referred to "drug responsiveness", e.g., "clopidogrel responsiveness").

Prior to the present invention, there was no readily available or accepted methodology to assess these patients; the invention provides such a methodology. More importantly, knowledge of a patient's platelet reactivity, TTF and TFF are invaluable in preventing complications related to surgical and percutaneous vascular procedures (e.g., stent placement or balloon angioplasty) such as stent thrombosis or re-stenosis. Furthermore, assessing risk of patients to thrombotic events provides a means to facilitate selection of therapy (e.g., dose, regimen, anti-platelet therapy, and the like) so as to better predict therapeutic efficacy.

The invention is based on the discovery that platelet reactivity, TTF and TFF provide a powerful and direct predictor of risk of serious complications in patients with vascular disease, such as acute thrombosis and myocardial infarction. In particular, the inventor has discovered that platelet reactivity, TTF and TFF directly predicts the occurrence of thrombosis in patients. For instance, platelet reactivity measured by ADP-induced aggregation and thrombin generation, as measured by thromboelastography (MA) directly correlates with the risk and occurrence of ischemic coronary events and coronary artery stent thrombosis.

The invention also addresses the need to provide a means to compile and correlate data from various assays that test various thrombosis and/or atherosclerosis risk factors. For example, the results of a platelet aggregation assay and assessment of risk as provided by the invention can be provided along with the results of various other assays so as to provide a patient's profile of risk for a thrombotic event (e.g., thrombosis and/or atherosclerosis). These methods can be implemented by a computer program which can be internet based, and which are designed to facilitate the use of the test results by medical professionals to have an enhanced understanding of the patient's individual profile and the most appropriate care to be administered.

The invention will now be described in more detail.

Thrombotic Events, Including Myocardial Ischemia

The methods and compositions of the invention can be used to assess risk of any of a variety of thrombotic events, including myocardial ischemic syndromes, including those associated with thrombosis and with atherosclerosis. Thrombotic events includes events such as heart attack (myocardial infarction, particularly acute myocardial infarction), stroke, cardiovascular death, angina, stent thrombosis, stent re-stenosis, deep venous thrombosis, pulmonary embolus, and the like.

The invention is the most immediate and direct assessment of a patient's risk for thrombosis (particularly stent thrombosis) and adverse ischemic events by measuring platelet reactivity, e.g., as assessed by platelet aggregation induced by ADP and thrombin, and/or TTF and/or TFF. Assessment of risk of thrombosis is of particular importance in determining a patient's risk prior to percutaneous therapy, particularly percutaneous therapy involving implantation of a stent. Thrombosis in this context can lead to a serious event that can and often does result in death during and after the procedure.

The methods of the invention find particular use in diagnosis and risk assessment of a variety of thrombotic or atherosclerotic events. Such thrombotic events include, but are not necessarily limited to myocardial infarction, particularly acute myocardial infarction. Acute myocardial infarction is death of myocardial tissue that is acute and secondary to occlusion of an artery that provides blood flow to the affected tissue. This can occur at any time.

Assessing Risk of a Thrombotic Event

The invention features methods for assessing a patient's risk of a thrombotic event (e.g., myocardial ischemia) by assessing platelet reactivity, and may also be assessed by assessing time-to-thrombin formation (TTF), and/or time-to-fibrin formation (TFF). The invention also features methods for assessing a patient's immediate risk of a thrombotic event (e.g., a thrombotic event such as myocardial ischemia, particularly a recurrent myocardial ischemia within about 6 months by assessing platelet reactivity, time-to-thrombin formation (TTF), and/or time-to-fibrin formation (TFF).

Commercially available devices and assays can be used to measure platelet reactivity, TTF, and TFF. These devices include light transmittance aggregometers (LTA); thromboelastography instruments (e.g., MA, R); single platelet counters (Plateletworks); flow cytometry to measure activation of platelets, microparticles and platelet-procoagulant activity (phosphatidyl-serine expression); methods to measure thrombosis after application of shear stress to a blood sample (Dade-Behring PFA-100); and methods to assess inhibition of platelets by specific drugs (aspirin and clopidogrel (Accumetrics)). Assessment of platelet reactivity, TTF and TFF can thus generally be accomplished in several different ways according to the invention.

In one embodiment, the method of the invention involves assessment of platelet reactivity to provide for a platelet reactivity score. This platelet reactivity score is analyzed to determine whether the platelet reactivity score is above, below or at a threshold value, where the threshold value demarcates a level of risk of a cardiac event, particularly a thrombotic event (e.g., stent thrombosis, myocardial ischemia, etc.). If a patient has a platelet reactivity score above a risk threshold value, then the patient is at an increased risk of, for example, stent thrombosis or myocardial. If a patient has a platelet reactivity score below a risk threshold value, then the patient has a decreased risk of, for example, stent thrombosis or myocardial ischemia. If a patient has a borderline or abnormal platelet reactivity score, then close monitoring of the patient is warranted.

Platelet reactivity can be assessed by any appropriate assay that assesses a change in function (e.g., induction of platelet aggregation), intracellular signaling pathways (e.g., VASP phosphorylation), or surface receptor expression (e.g., GP IIa/IIIb expression; p-selectin; PCAM-I, CD40 ligand, and the like) in the presence of a stimulus associated with clot formation. Methods for assessing platelet reactivity in terms of a change in function, intracellular signaling pathways, or surface receptor expression are well known the art.

For example, in one embodiment, platelet reactivity is assessed through an ADP-induced platelet aggregation assay. Methods for conducting such assays are well known in the art, and examples of the use of such assays are detailed in the Examples section below.

In general, the platelet aggregation assay is conducted to provide a platelet aggregation score. As used herein, a "platelet aggregation score" ("PA score"), is defined as a measure of the reactivity of platelets to various stimuli. Because the PA score value varies according to the conditions under which the assay is conducted, "PA-Xn" refers to a PA score determined in the presence of a stimulant "X", where "n" represents the concentration of the stimulant, where relevant (e.g., ADP at concentration of "n" μM). For example, "PA-ADP5" refers to a PA score determined in the presence of 5 μM ADP, while PA-ADP20 refers to a PA score determined in the presence of 20 μM ADP.

A patient's PA score is compared to a risk threshold PA score. If the patient PA score is greater than a risk threshold PA score, then the patient is at an increased risk of a thrombotic event. If the PA score is lower than a risk threshold PA score, then the patient has a lower risk of a thrombotic event. Because the platelet aggregation assay can be sensitive to the concentration of ADP used to induce aggregation, the risk threshold differs according to the ADP concentration used in the assay.

In another exemplary embodiment, platelet reactivity is assessed by thromboelastography Maximum Amplitude (MA), which reflects strength of a clot, which in turn is dependent on number and function of platelets and its interaction with fibrin. In general, the thromboelastography is an available viscoelastic tests that characterizes formation and strength of the blood clot over time, and can be used to measure in vitro and ex vivo the life of a clot, the time to initial clot formation (time to thrombin generation or time to fibrin generation), then evaluate the acceleration phase of the developing clot, as well as its strengthening and retraction. Thromboelastography can also be used to detect clot lysis.

Methods for assessing platelet reactivity by thromboelastography are known in the art. In general, a sample of activated whole blood is placed into a container such as a cuvette, and a suspended piston lowered into the cuvette and is moved in rotation of a 4.5 degree arc backwards and forwards. The fiber strands which interact with activated platelets attach to the surface of the cuvette and the suspended piston. The clot forming in the cuvette transmits its movement onto the suspended piston. A "weak" clot stretches and therefore delays the arc movement of the piston, which is graphically expressed as a narrow thromboelastography. A strong clot in contrary will move the piston simultaneously and proportionally to the cuvettes movements, creating a thick thromboelastography. There are five parameters of the thromboelastography tracing: R, k, alpha angle, MA and MA60, which measure different stages of clot development. R (reaction time) is a period of time from initiation of the test to the initial fibrin formation; k is measure of time from beginning of clot formation until the amplitude of thromboelastography reaches 20 mm, and represents the dynamics of clot formation. The alpha angle is an angle between the line in the middle of the thromboelastography tracing and the line tangential to the developing "body" of the thromboelastography tracing. The alpha angle represents the acceleration (kinetics) of fibrin build up and cross-linking. MA is the Maximum Amplitude and reflects strength of a clot, which in turn is dependent on number and function of platelets and its interaction with fibrin. The MA60 is a measure of the rate of amplitude reduction 60 min. after MA and represents the stability of the clot. In general, as used herein thromboelastography values are provided as MA values.

Additional examples of assessing platelet reactivity are provided in the Examples section below. In general, platelet reactivity can be assessed by any appropriate assay that assesses a change in function (e.g., induction of platelet aggregation), intracellular signaling pathways (e.g., VASP phosphorylation), or surface receptor expression (e.g., GP IIa/IIIb expression; p-selectin; PCAM-I, CD40 ligand, and the like) in the presence of a stimulus associated with clot formation. Methods for assessing platelet reactivity in terms of a change in function, intracellular signaling pathways, or surface receptor expression are well known the art.

Selection of the appropriate assay will generally depend upon the circumstances for which risk of a thrombotic event is to be assessed, and will be readily apparent to the ordinarily skilled artisan upon reading of the present disclosure. For example, where the risk of a thrombotic event such as a stent thrombosis is to be assessed, assessing platelet reactivity by examining change in platelet function (e.g., by platelet aggregation (e.g., in the presence of ADP), but preferably not by thromboelastography MA) is of particular interest. Where the immediate risk of a thrombotic event (such as recurrent ischemia) is to be assessed, assessing platelet reactivity (e.g., by platelet aggregation (e.g., in the presence of ADP) or by thromboelastography (e.g., thromboelastography MA)), by assessing TTF, or by assessing TFF (where thromboelastography R provides a measure of both TTF of particular interest.

Risk of Thrombotic Event

In one embodiment, the invention is based on the discovery that occurrence of adverse thrombotic events, particularly after percutaneous intervention (e.g., percutaneous coronary revascularization), is related to platelet reactivity (e.g., as measured by change in platelet function (e.g., platelet aggregation in the presence of ADP), change in intracellular signaling (e.g., VASP phosphorylation), or by change in platelet receptor expression (e.g., expression of GP IIb/IIIa)), with the proviso that platelet reactivity is assessed by a method other than thromboelastography MA. For example as described herein, studies of patients who have suffered subacute thrombosis (SAT) show that mean platelet reactivity is higher than in those patients who were free of this adverse event.

Figure 2:
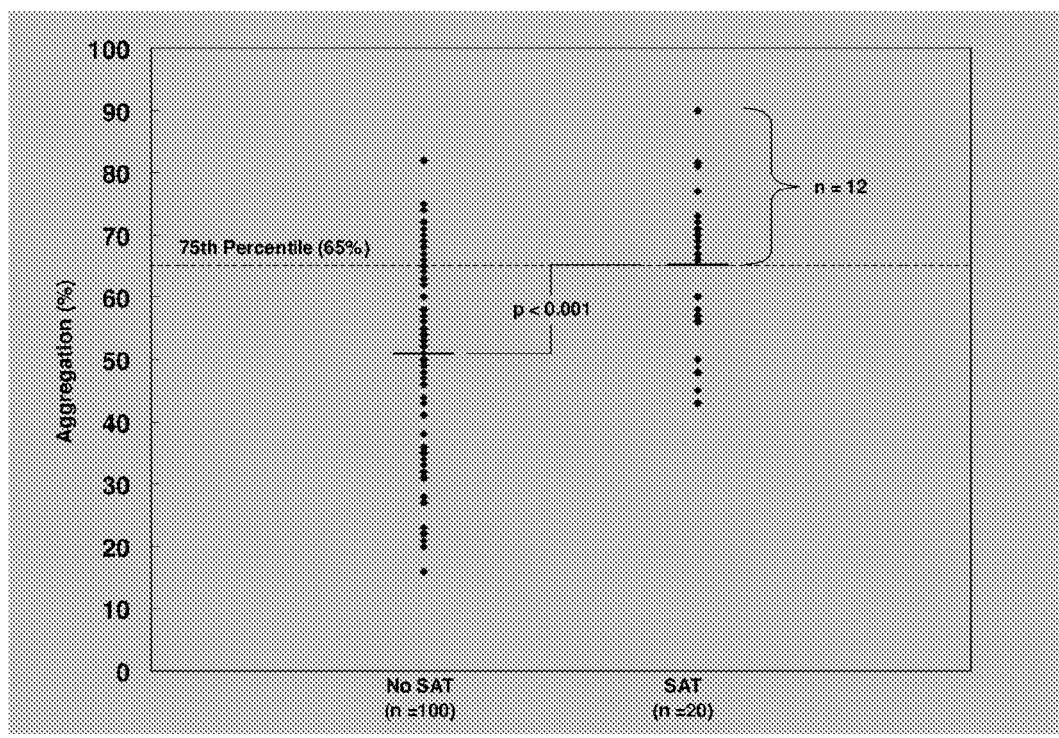
FIG. 2 is a graph showing ADP-induced Platelet aggregation (20 µM) in patients with stent thrombosis (SAT) and without stent thrombosis (No SAT).
Figure 3:
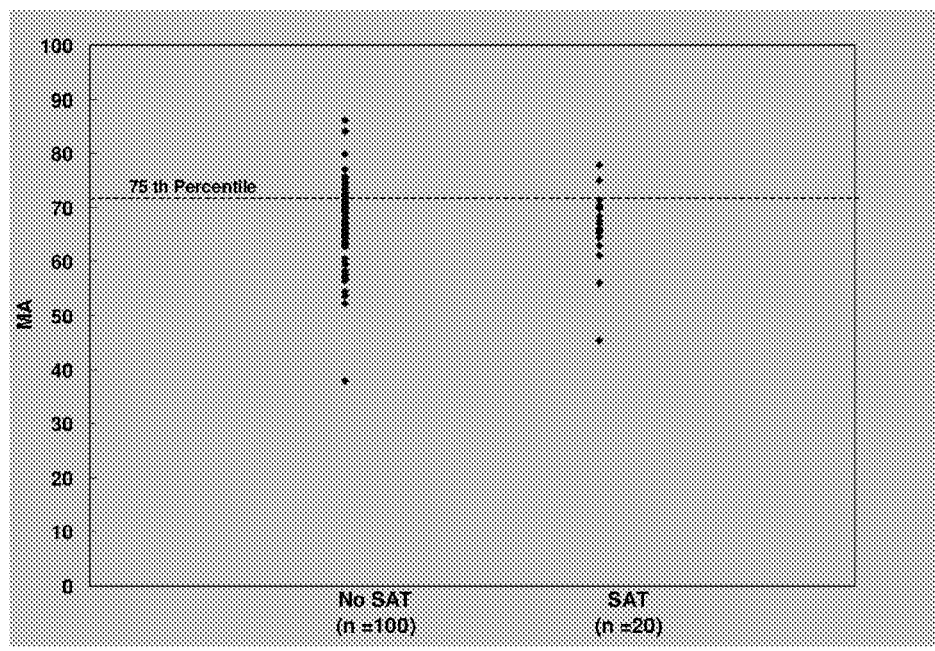
FIG. 3 is a graph showing thromboelastography MA analysis in patients with stent thrombosis (SAT) and without stent thrombosis (No SAT).

For example, in one embodiment, platelet reactivity as assessed by ADP-induced platelet aggregation. In general, a threshold of about 30% or greater, platelet aggregation induced by 5 μM ADP (that is, a PA-ADP5 score of about 30% or greater) defined about 80% of the patients with stent thrombosis (SAT) (FIG. 1). A threshold of about 42% or greater, platelet aggregation induced by 20 μM ADP (that is, a PA-ADP20 score of about 42% or greater) included about 100% of the patients with SAT, while and a threshold of about 50% or greater, platelet aggregation induced by 20 μM ADP (a PA-ADP20 score of about 50% or greater) defined about 80% of the patients with SAT (FIG. 2). Thus the risk threshold for aggregation to define about 80% of SAT events is a PA-ADP5 score of about 30% or greater or a PA-ADP20 score of about 50% or greater. In contrast, measurement of platelet reactivity as assessed by thromboelastography MA was not as reliable a predictor of SAT (FIG. 3). Thus, where the risk of a patient for stent thrombosis is to be assessed (e.g., prior to surgery), platelet reactivity should be assessed using an assay other than thromboelastography MA (e.g., platelet aggregation in the presence of ADP).

Specifically, Example 1 below illustrates that patients who had a platelet aggregation (5 μM ADP) (PA-ADP5) score of 49±4% suffered a SAT while patients who had a PA-ADP5 of 26±2% did not have SAT (p<0.001, n=120 pts). Patients who had a platelet aggregation (20 μM ADP) (PA-ADP20) score of 65±3% suffered SAT while patients who had a PA-ADP20 of 46±2% did not (p<0.001, n=120 pts).

Example 2 below shows that the absence of infarcts in patients undergoing elective PCI with lower than about 50% mean 5 μM ADP-induced aggregation indicates a threshold effect. Thus a 5 μM ADP-induced platelet aggregation score of less than about 50%, regardless of the percent reduction relative to pretreatment platelet aggregation, is a therapeutic target to which therapy should be tailored. (n=120 patients)

Thus a risk threshold value for platelet reactivity as assessed by PA-ADP5 is defined as being from about 24% to 36%, usually about 26% to 34%, usually about 28% to 32%, usually about 30%, and can be about 24%, 25%, 26%, 27%, 28%, 29%, 30%, 31%, 32%, 33%, 34%, 35%, or 36%, more usually about 30%. A PA-ADP5 score above this PA-ADP5 risk threshold value indicates an increases risk of a thrombotic event such as stent thrombosis in the patient.

A risk threshold value for platelet reactivity as assessed by PA-AD20 is defined as being from about 40% to 60%, usually about 42% to 58%, usually about 46% to 56%, usually about 48% to 54%, usually about 40%, 41%, 42%, 43%, 44%, 45%, 46%, 47%, 48%, 49%, 50%, 51%, 52%, 53%, 54%, 55%, 56%, 57%, 58%, 59% or 60%, more usually about 50%. A PA-ADP20 score about this PA-ADP20 risk threshold score indicates an increased risk of a thrombotic event such as stent thrombosis.

In another embodiment, risk of a thrombotic event (e.g., stent thrombosis) is assessed by a change in intracellular signaling, e.g., as assessed by VASP phosphorylation. As described in the Examples below, a $P2Y_{12}$ reactivity ratio can be calculated to assess VASP phosphorylation. A $P2Y_{12}$ reactivity ratio of 46±9 was associated with no SAT within 6 months, while a $P2Y_{12}$ reactivity ratio of 69±5 was associated with SAT within about 6 months (Table 3). Thus a risk threshold value for $P2Y_{12}$ reactivity ratio is defined as a $P2Y_{12}$ reactivity ratio of from about Thus, a $P2Y_{12}$ reactivity ratio score of from about 32 to about 48, from about 34 to 46, from about 36 to 44, from about 38 to 42, usually about 32, 33, 34, 35, 36, 37, 38, 39, 40, 41, 42, 43, 44, 45, 46, 47, or 48, more usually about 40. A $P2Y_{12}$ reactivity ratio score above this $P2Y_{12}$ reactivity ratio risk threshold value indicates an increased risk of a thrombotic event such as stent thrombosis in the patient.

In another embodiment, risk of a thrombotic event (e.g., stent thrombosis) is assessed by a change in receptor expression, e.g., as assessed by GP IIb/IIIa expression (e.g., as assessed by surface receptor density). As described in the Examples below, a stimulated GP IIb/IIIa expression level of 42±4 was associated with no SAT within 6 months; a stimulated GP IIb/IIIa expression level of 138±19 was associated with SAT within 6 months (Table 3). Thus a risk threshold value for stimulated GP IIb/IIIa expression is defined as a stimulated GP IIb/IIIa expression of from about 32 to about 48, from about 34 to 46, from about 36 to 44, from about 38 to 42, usually about 32, 33, 34, 35, 36, 37, 38, 39, 40, 41, 42, 43, 44, 45, 46, 47, or 48, more usually about 40. A stimulated GP IIb/IIIa expression score above this stimulated GP IIb/IIa expression risk threshold value indicates an increased risk of a thrombotic event such as stent thrombosis in the patient.

Assessment of Immediate Risk of a Thrombotic Event

In another aspect, the invention provides for assessment of immediate risk of a thrombotic event, particularly an ischemic event, such as stroke, recurrent angina, and the like. In this aspect, risk can be assessed by examining platelet reactivity, TTF, or TFF. By "immediate risk" as used herein is meant risk of a thrombotic event, particularly a recurrent thrombotic event (e.g., recurrent myocardial ischemia) within a period of months from the time of the assay (e.g., within about 3, 4, 5, 6, 7, 8, 9, 10, 11, 12, 13, 14, 15, 16, 17, or 18 months, usually within 4 months to 12 months, more usually within 6 months to 12 months, still more usually within 6 months from the time of the assay). In some embodiments it may be desirable to assess immediate risk of a thrombotic event using one or more of such methods.

As discussed in the examples below in more detail, in patients whose platelet reactivity and TTF/TFF (as assessed by thromboelastography R) was measured at discharge following percutaneous coronary revascularization. As discussed in the Examples below, platelet reactivity (e.g., as assessed by platelet aggregation and thromboelastography by the thromboelastography (MA)), as well as TTF and TFF (e.g., as assessed by thromboelastography R), are powerful predictors for the occurrence of adverse ischemic events within 6 months.

Figure 17:
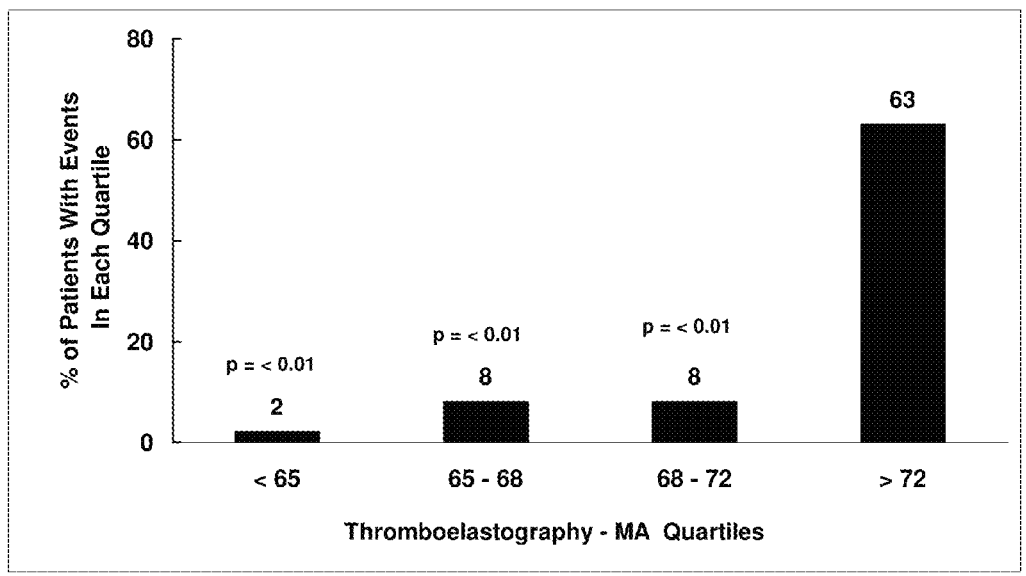
FIG. 17 is distribution of patients with events into quartiles and the incidence of events in each quartile as measured by maximum amplitude (thromboelastography MA) P values are in comparison with highest quartile.

For example, in a study of 192 patients about 63% of patients in the highest MA quartile (at least about 72 thromboelastography (MA) score, usually greater than about 72 thromboelastography (MA) score) will have an ischemic event within 6 months of discharge as compared to about 8% in the second quartile, about 8% in the third quartile and about 2% in fourth highest quartile (FIG. 17). Thus, a threshold defining the highest two quartiles (MA of about 68 or greater) includes about 85% of all patients having an ischemic event within a 6 month period. Thus a thromboelastography MA score of about 58 to 86, usually about 60 to 84, usually about 62 to 82, usually about 64 to 80, more usually about 66 to 78, usually about 66 to 78, usually about 68 to 76, usually about 69 to 74, usually about 71 to 73, more usually about 58, 59, 60, 61, 62, 63, 64, 65, 66, 67, 68, 69, 70, 71, 72, 73, 74, 75, 76, 77, 78, 79, 80, 81, 82, 83, 84, 85, or 86, generally about 72 defines a risk threshold value for assessing immediate risk of a thrombotic event in a patient.

Figure 15:
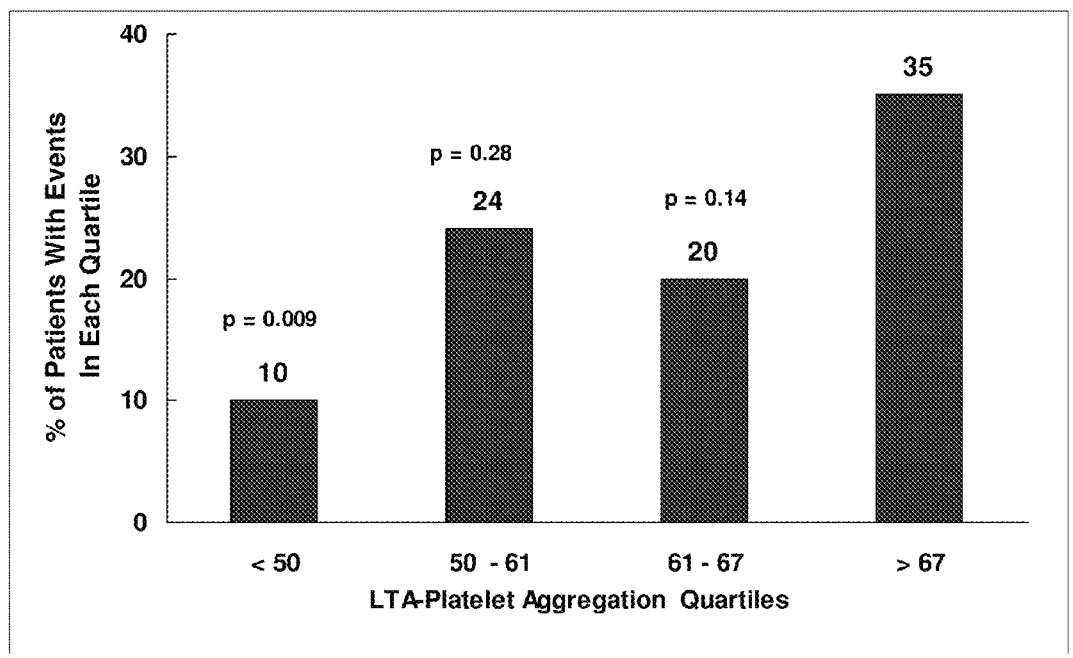
FIG. 15 is a distribution of patients with events into quartiles and the incidence of events in each quartile as measured by light transmittance aggregometry (20 uM ADP). P values are in comparison with highest quartile.

Platelet reactivity as assessed by ADP-induced platelet aggregation was also a reliable predictor of risk of an ischemic event within about 6 months. Of the patients examined in the studies described herein, about 35% of patients in the highest aggregation (20 μM ADP) quartile (greater than about 67% PA-ADP20) will have an ischemic event within 6 months of discharge as compared to 20%, 24%, and 10% in the second, third, and fourth highest quartiles, respectively (FIG. 15). Thus, using the threshold defining the highest two quartiles (PA-ADP20 of about 61% or greater) will include about 60% of all of those patients having an ischemic event within about 6 months.

Figure 11:
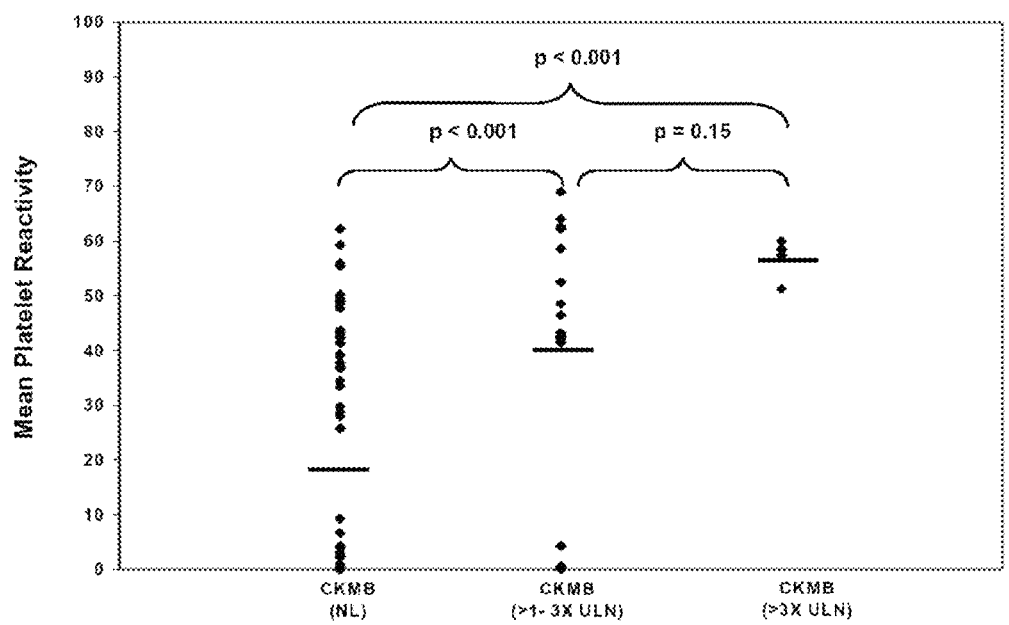
FIG. 11 is a graph showing the relation of necrosis marker release (CKMB) to mean platelet reactivity as measured by 5 M ADP-induced aggregation. NL=normal limit; ULN=upper limit of normal value.
Figure 12:
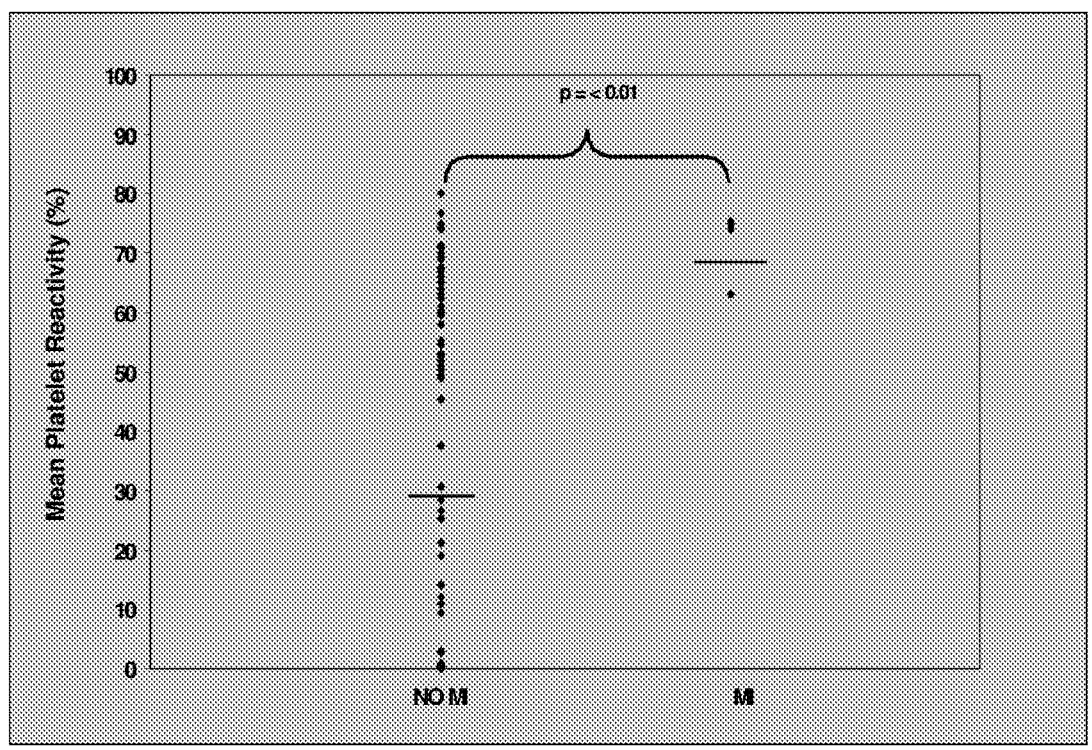
FIG. 12 is a graph showing the relation of myocardial infarction to mean platelet reactivity as measured by 20 µM ADP-induced aggregation.

Finally, in patients whose platelet reactivity was measured serially while in hospital following percutaneous revascularization (PCI), as illustrated herein development of myocardial infarction is dependent on platelet reactivity. Using a threshold of about 50% 5 μM ADP-induced aggregation included all of those patients who suffered a myocardial infarction (CKMB>3× upper limits normal) (FIG. 11). Using a threshold of about 64% 20 μM ADP-induced aggregation included all of those patients who suffered a myocardial infarction (CKMB>3× upper limits normal) (FIG. 12).

Thus, a PA-ADP5 score of about 45% to 55%, 47% to 53%, 49% to 51%, usually about 45% 46%, 47%, 48%, 49%, 50%, 51%, 52%, 53%, 54%, or 55%, usually about 50% defines a risk threshold value for assessing immediate risk of a thrombotic event particularly a recurrent thrombotic event such as myocardial ischemia, in a patient.

Further, a PA-ADP20 score of from about 52% to 76%, usually about 54% to 75%, usually from about 56% to 73%, usually from about 58% to 71%, usually from about 60% to 69%, usually about 62% to 67%, usually about 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, or 76%, more usually about 64% defines a risk threshold value for assessing immediate risk of a thrombotic event particularly a recurrent thrombotic event such as myocardial ischemia, in a patient.

Figure 19:
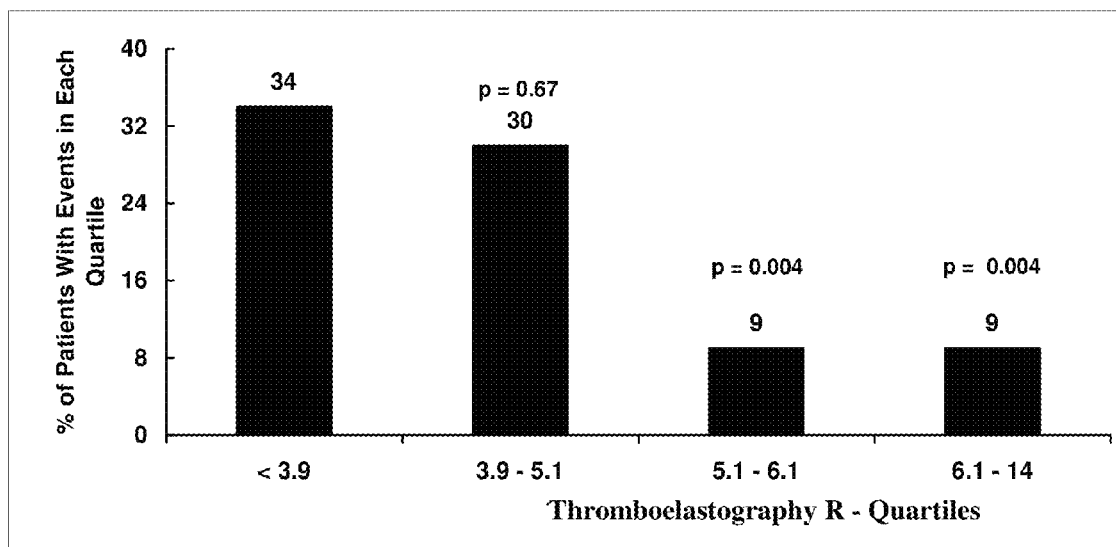
FIG. 19 is distribution of patients with events into quartiles and the incidence of events in each quartile as measured by Reaction Time (thromboelastography R) P values are in comparison with lowest quartile.

In another embodiment, assessment of immediate risk of a thrombotic event, particularly an ischemic event by examining TTF or TFF. Methods for assessing TTF and TFF are well known in the art. In one embodiment, thromboelastography R (a period of time from initiation of the test to the initial fibrin formation) is used. Since fibrin formation is dependent upon thrombin formation, thromboelastography R can be used to approximate both TTF and TFF. As described in the Examples in more detail below, a thromboelastography R score of less than about 5.1 minutes indicates the patient is at risk of a thrombotic event within about 6 months (FIG. 19). Thus a TFF score, and thus a TTF score, of from about 4.6 min to 5.6 min, usually from about 4.8 min to 5.4 min, usually from about 4.9 min to 5.2 min, usually about 4.6 min, 4.7 min, 4.8 min, 4.9 min, 5.0 min, 5.1 min, 5.2 min, 5.3 min, 5.4 min, 5.5 min, or 5.6 min, usually about 5.1 min defines a risk threshold value for assessing immediate risk of a thrombotic event, particularly a recurrent thrombotic event such as myocardial ischemia, in a patient.

Depending on the event to be assessed (e.g., SAT vs recurrent ischemia vs post-elective PCI myocardial infarction (MI)), based on the extensive collection of data provided herein, applying thresholds of platelet aggregation by 5 µM and 20 µM ADP and thromboelastography can define high risk groups. The data summarized above and described in more detail below support the utility of both methodologies, specifically conventional platelet aggregation to define high risk for SAT and peri-procedural MI, and the thromboelastography to define high risk for events within 6 months of PCI.

Where platelet aggregation is assessed in the context of therapy, such as an anti-platelet therapy (e.g., clopidogrel), platelet aggregation is assessed without regard to (i.e., independent of) a pretreatment baseline of platelet aggregation. The invention is based on the discovery that high platelet reactivity and low TTF/TFF is associated with a high risk of an ischemic event, e.g., a thrombotic event, regardless of whether the values obtained reflect a patient who is responsive or non-responsive to therapy (e.g., regardless of whether platelet reactivity is reduced in response to administration of drug, e.g., an anti-platelet inhibitor such as clopidogrel).

When a patient's PA score is greater than the corresponding risk threshold, then the patient is diagnosed as having a risk of thrombosis, which can result in acute myocardial infarction, myocardial ischemia, restenosis, or stroke.

Patients can be stratified into ranges based on inter-quartile levels and stratified according to risk. In general, patients in or above the 75th percentile for platelet aggregation have a high risk of subsequent adverse ischemic events within six months after coronary artery stenting. The data presented in the present specification indicate that patients within at least the 75$^{th}$ percentile (the first quartile for ADP-induced aggregation or by thromboelastography) are at about a 35-63% % risk of a thrombotic event within 6 months. Patients with ADP-induced platelet aggregation of at least about 50% by 5 µM ADP or at least about 64% by 20 µM ADP post-percutaneous intervention (PCI) are at risk for myocardial infarction (MI) in-hospital. Below these thresholds no infarcts were observed.

Diagnosis as to the particular type of myocardial ischemic condition relevant to the patient can be made based on clinical signs and symptoms, generally clinical signs or symptoms that distinguish among conditions associated with myocardial ischemic conditions.

The assessment of risk of SAT or MI in the patient can then be incorporated into a regimen of care for the patient. For example, if a patient is above a risk threshold for SAT, then the clinician can assess the risk and benefits of alternate therapies and further consider an anti-thrombotic regimen. If a patient is below a risk threshold for SAT, then administration of anti-thrombotics (e.g., clopidogrel) may be unnecessary or may be administered in lower doses. If a patient is borderline or abnormal, then the clinician can assess the risk and benefits of alternate therapies and further consider an anti-thrombotic regimen.

It is noted that platelet reactivity, TTF, or TFF prior to treatment (e.g., by administration of an anti-thrombotic such as clopidogrel) determines post-treatment reactivity, TTF, or TFF following coronary artery stenting. Thus, for example, a pre-treatment platelet aggregation score may provide an indicator of the type and extent of follow-up therapy that is warranted.

Similarly, if a patient is above a risk threshold for myocardial ischemia within 6 months, then the clinician can assess the risk and benefits of initiating therapy or modifying a current therapy. If a patient is below a risk threshold for myocardial ischemia within 6 months, then initiation or modification of therapy is not warranted. If a patient is borderline or abnormal then more close monitoring of the patient is warranted.

Coordinated Diagnosis of Risk of Myocardial Ischemia Based on Profile of Markers: the Thromboprofile™

In one embodiment, the invention provides development of a myocardial ischemia risk profile, particularly a thrombotic risk profile and/or atherosclerosis risk profile, for a patient having or suspected of having vascular disease. Such a "ThromboProfile™" is used with the goal of detecting patients at risk for atherosclerosis, thrombosis, and/or bleeding in order to reduce morbidity and mortality. A "Thrombo-Profile™" provides a direct, immediate and accurate risk assessment available thus circumventing estimates provided by more traditional and indirect measurements of thrombosis risk noted previously.

Any number of risk factors assessed by a variety of different assays can be included in the profile analysis. Risk factors that can be included in the myocardial ischemia risk profile include, but are not necessarily limited to lipid risk factors (e.g., cholesterol level, LDL cholesterol level, LDL cholesterol particle size, HDL cholesterol level, HDL cholesterol particle size, triglyceride level, LPa, Lp-PLA2, and the like), markers of inflammatory risk factors (e.g., levels of markers such as, e.g., C-reactive protein, Interleukin-6, and myeloperoxidase), markers of oxidation risk factors (e.g., myeloperoxidase, oxidized LDL, oxidized fatty acids, and the like), metabolic risk factors (e.g., glucose measurements (e.g., as measured by fasting glucose levels, hemoglobin A1C (glycosylated hemoglobin), homocysteine levels, and the like), platelet reactivity analysis (ADP-induced aggregation (e.g., at 5 µM and/or 20 µM), thromboelastography (MA), VASP-P, platelet receptors (e.g., GP IIa/IIIb, and the like), and other measures of platelet reactivity), coagulation risk factors (e.g., as assessed by thromboelastography analysis prothrombin time (PT), INR, fibrinogen levels, platelet count, and the like) and responsiveness to anti-platelet therapy (e.g., clopidogrel response, aspirin response, and the like), and homocysteine levels. Values provided in the table below are merely exemplary of values for assays for these factors, which assays and values are in the art, and which values may vary, e.g, according to differences in assays (e.g., sensitivity of assays

| | Desired Level | Disease Level | | At risk |
|---|---|---|---|---|
| Lipid Risk Factors | | | Platelet Reactivity | |
| Total Cholesterol | <200 mg/dl | >200 mg/dl | Aggregation (LTA) (5 uM) | >26% SAT |
| LDL Cholesterol | <130 mg/dl | >130 mg/dl | Aggregation (LTA) (20 uM) | >45-50% SAT >50% I |
| HDL Cholesterol | >40 mg · dl | <40 mg/dl | Thromboelastography MA | >68 I |
| Triglycerides | <150 mg/dl | >150 mg/dl | P2Y12 React | >46% |
| LDL Particle Size | Small dense LDL absent | Small dense LDL present | Receptors | >42 MFI |
| LDL Particle Concentration | <1100 nanomol/l | >1100 nanomol/l | React time | <5.1 I |
| HDL Particle Size | large | small | Coragulation Thromboelastography analysis (reaction time) | <5.1 I |
| HDL Particle Concentration | >30 mg/dl | <30 mg/dl | | |
| LPa | <10 mg/dl | >10 mg/dl | | |
| Inflammation Risk Factors | | | | |
| HS-CRP | <1 mg/dl | >1 mg/L | | |
| IL-6 | <1.08 pg/ml | ≥2.92 pg/ml | | |
| ICAM-1 | <267.8 ng/ml | >285.2 ng/ml | | |
| Metabolic Risk Factors | | | Tailored therapy* | |
| Fasting glucose | 70-110 mg/dl | >110 mg/dl | Clopidegrel | |
| Hemoglobin A1C | 4.5%-5.70% | >6.0% | Aspirin | |

I = ischemia,
SAT = subacute stent thrombosis
*Tailored Therapy: Patients on clopidogrel should target 5 microM <26% or 20 microM <45%. If not at target, consider increased dose or alternative therapy. Aspirin aggregation by arachidonic acid target is: <5% for aspirin responders. If aspirin non-responsive consider increased dose or alternative therapy.

In one embodiment, values associated with lipid risk factor assays, inflammation risk factors, oxidation markers, and metabolic risk factors are assessed to provide an atherosclerotic profile. In another embodiment, platelet reactivity assays, coagulation assays, and responsiveness to anti-platelet drugs, are assessed to provide a thrombotic profile.

In general, cholesterol levels (including total cholesterol, LDL, HDL, particle sizing), triglyceride levels, glucose measurements and homocysteine levels assess the risk for atherosclerosis and arterial plaque formation. These indirect markers are used to assess risk of myocardial infraction.

The profiles generated according to the invention can be used in a variety of settings. For example, coagulation status can be used to assess the bleeding risk in patients on anticoagulants and in the peri-operative window. For instance, inhibitors of coagulation (warfarin (coumadin) and heparin) are often used as "blood thinners" and are monitored by PT and INR.

The risk profile does not assume that patients with atherosclerosis or thrombosis are similar or should be treated in a similar manner. Instead, the patients are individually graded according to risk based on one or more of these markers. In particular, platelet reactivity, particularly platelet aggregation, is an important, yet currently ignored, factor.

The results of assessment of various risk factors can be provided as a "scorecard" as exemplified above. In one embodiment, one or more assays are conducted and provided on such a scorecard. In another embodiment, the scorecard is provided as a display on a device (e.g., handheld device, computer desktop, website) that results from execution of a computer program to provide an electronic or "virtual" scorecard, as displayed above.

Manual and Computer-Assisted Methods and Products
Computer Program

The values from the assays described above, such as the platelet reactivity score (e.g., platelet aggregation score or thromboelastography MA score), TTF score, and TFF score (e.g., where TTF and TFF are assessed by thromboelastography R), can be calculated and stored manually, e.g., on a physical scorecard as exemplified above. Alternatively, the above-described steps can be completely or partially performed by a computer program product. The present invention thus provides a computer program product including a computer readable storage medium having a computer program stored on it. The program can, when read by a computer, executes relevant calculations based on values obtained from analysis of one or more biological sample from an individual (e.g., of changes in values associated with therapy (e.g., a pretreatment value vs. a posttreatment value and/or values obtained at times $t_1$ and $t_2$ over a selected period, e.g., during administration of a therapeutic regimen), conversion of values from assays to a score above or below a selected threshold, and the like) The computer program product has stored therein a computer program for performing the calculation.

Figure 20:
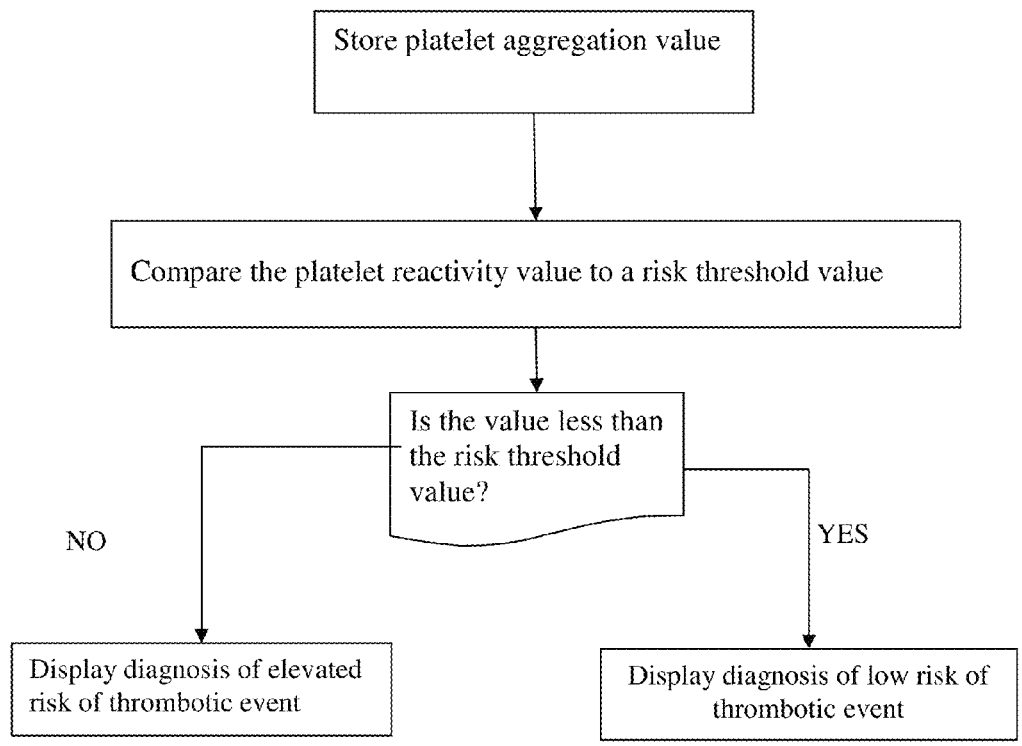
FIG. 20 is a flowchart exemplifying the computer program of the invention.

The computer program product can also analyze the data, as depicted in FIG. 20, wherein a value for an assay result is determined; and the computer program product then determines whether the value is above or below a pre-determined value, e.g., a risk threshold value. For example, in the context of assessing risk of a thrombotic event by assessing platelet aggregation, a platelet aggregation score or value is compared to a risk threshold value, e.g., 50% 5 μM ADP-induced platelet aggregation (e.g., as assessed by LTA). Based comparison to the threshold value, the computer program product assesses the risk of thrombosis in the patient, and displays a result to the user. The values for analysis by the computer program can be input into the program manually, or the values can be obtained from an assay device (e.g., the values obtained by a light transmission aggregometer (LTA) device) can be transferred directly into the program so as to avoid manual input.

In other embodiments, the computer program is designed to store values for 1, 2, 3, 4, 5, 6, 7, 8, 9, 10 or more different assays associated with the ThromboProfile™ described above. In one embodiment, and in a manner similar to that described above in the context of a platelet aggregation assay, the program analyzes one or more of these assay values to determine whether the value is above or below a pre-determined value, e.g., a threshold value, such as a risk threshold value. Based comparison of an assay value to the corresponding threshold value for that assay, the computer program product assesses the risk in the patient, and displays a result to the user. The values for analysis by the computer program can be input into the program manually, or the values can be obtained from an assay device.

Exemplary assay values which can be included in the invention include values obtained from assay(s) of one or more of lipid risk factors (e.g., total cholesterol, LDL cholesterol, HDL cholesterol triglycerides, LDL particle size, HDL particle size, LDL concentration, HDL particle size, HDL particle size, LPa, Lp-P)LA2, and the like), inflammation risk factors (e.g., HS-CRP, IL-6, ICAM-6), oxidation markers (e.g., myeloperoxidase, oxidized LDL, oxidized fatty acids, and the like), metabolic risk factors (fasting glucose, hemoglobin A1C, and the like), platelet reactivity (e.g., aggregation (e.g., by 5 μM ADP- and/or 20 μM ADP-induced aggregation), thromboelastography analysis, VASP-P, platelet receptors (e.g., GP IIa/IIIb, and the like), and other measures of platelet reactivity), coagulation (e.g., thromboelastography analysis and the like), and responsiveness to anti-platelet therapy (e.g., clopidogrel response, aspirin response, and the like). In one embodiment, values associated with lipid risk factor assays, inflammation risk factors, oxidation markers, and metabolic risk factors can be displayed separately as values relating to risk of atherosclerosis. Similarly, values associated with platelet reactivity assays, coagulation assays, and responsiveness to anti-platelet drugs (e.g., clopidogrel, aspirin, and the like) can be displayed separately as risk factors for thrombosis.

Optionally, the program can store multiple values from multiple different assays and/or from the same assays conducted at different times. The program can also store multiple risk assessment calculation results so as to provide a picture of the patient's thrombotic risk over time (e.g., during a course of therapy). In addition, the program can store any of a variety of patient information details (e.g., patient vitals and statistics, treatment history (particularly with respect to therapy administered at the time of an assay for which an assay value and/or risk assessment calculation is stored), and the like).

Systems and Apparatus

In a related embodiment, the invention provides a system for executing the program described above, which system generally includes: a) a central computing environment; b) an input device, operatively connected to the computing environment, to receive patient data, wherein the patient data can include, for example, a platelet aggregation score or value or other value obtained from an assay using a biological sample from the patient as described in detail above; c) an output device, connected to the computing environment, to provide information to a user (e.g., medical personnel); and d) an algorithm executed by the central computing environment (e.g., a processor), where the algorithm is executed based on the data received by the input device, and wherein the algorithm calculates a risk of a thrombotic event, e.g., by comparing a platelet aggregation score to a threshold value associated with risk of thrombosis, including risk of acute myocardial infarction, where a platelet aggregation score above the threshold value indicates risk of thrombosis within a period in the future, e.g., within 3, 4, 5, 6, 7, 8, 9, 10, 11, 12, 13, 14, 15, 16, 17, or 18 months, usually within 4 months to 12 months, more usually within 6 months to 12 months, still more usually within 6 months from the time of the assay.

The instant invention further provides a portable apparatus having a computer readable medium (e.g., a processor) that stores data, calculates risk based on the algorithm described above, and provides an assessment of risk of a thrombotic event based on the calculation. The portable apparatus can also store multiple values and risk assessment calculation results so as to provide a picture of the patient's thrombotic risk over time (e.g., during a course of therapy).

In some embodiments, a subject apparatus (e.g., a portable apparatus) comprises: a) a device for receiving and storing patient data as described above, including assay values, calculation results, and patient information; b) a data output device; and c) an algorithm stored within the computer program product within the apparatus, which algorithm, for example, assesses risk of a thrombotic event based on a platelet aggregation score compared to a risk threshold value, which information is transmitted to the data output device, where the output device displays the information (e.g., "high risk of thrombosis" or "low risk of thrombosis") to a user.

The data input device (also referred to as an operator input device) may be, e.g., a keyboard, a mouse, and the like. The processor has access to a memory, which may be any suitable device in which the processor can store and retrieve data, such as magnetic, optical, or solid state storage devices (including magnetic or optical disks or tape or RAM, or any other suitable device). The processor can include a general purpose digital microprocessor (such as is typically used in a programmable computer) suitably programmed to execute an algorithm as described above, or any hardware or software combination which will perform the required functions.

In some embodiments, the processor will be programmed to calculate the risk of thrombosis based on a platelet aggregation score obtained from a biological sample from an individual. The information will be transmitted to the output device for display to a user. The information will in some embodiments be displayed as "high risk of thrombotic event" or "low risk of thrombotic event," although alternative language is possible.

In some embodiments, the portable apparatus comprises: a) a device for determining an assay value (e.g., a platelet aggregation score) from a biological sample; b) a device for communicating (e.g., transmitting) the determined value to the receiving and storage device; c) a device for receiving and storing patient data, where the data can include, for example, the age of the patient, the gender of the patient, prior cardiac history, history of therapy (including percutaneous and non-percutaneous (e.g., drug) intervention) and values obtained from assays conducted with a biological sample from the patient; d) a data output device; and e) an algorithm stored within a computer program product within the apparatus, which algorithm is executed to, for example, determine whether a platelet aggregation score or value is above or below a risk threshold value; and assess risk of a thrombotic event in the patient. The result is transmitted to the data output device, where the output device displays the assessment to a user, which assessment can optionally include the platelet aggregation value, the risk threshold value used, or both. Suitable devices for determining a value for an assay results for the assays described above are well known in the art. For example, where the assay is an ADP-induced platelet aggregation assay, the device can be a light transmission aggregometer.

In general, a subject apparatus will include a computer readable medium including the programming described above. The computer program can be recorded on computer readable media, e.g., any medium that can be read and accessed directly or indirectly by a computer. Such media include, but are not limited to: magnetic tape; optical storage such as compact disc-read only memory (CD-ROM) and digital versatile disk (DVD); electrical storage media such as random access memory (RAM) and read-only memory (ROM); and hybrids of these categories such as magnetic/optical storage media. One of skill in the art can readily appreciate how any suitable computer readable media can be used to create a manufacture that includes a recording of the present programming/algorithms for carrying out the above-described methodology. In certain embodiments, the programming is further characterized in that it provides a user interface, where the user interface presents to a user the option of selecting among one or more different, including multiple different, criteria, e.g., age of individual, etc. The instructions may include installation or setup directions. The instructions may include directions for use of the invention.

In addition, a subject apparatus will typically include instructions for using the apparatus to carry out a subject method. The instructions of the above-described apparatus are generally recorded on a suitable recording medium. For example, the instructions may be printed on a substrate, such as paper or plastic, etc. As such, the instructions may be present in the apparatus as a package insert, or components thereof (i.e. associated with the packaging or sub packaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the apparatus, but means for obtaining the instructions from a remote source, e.g. via the Internet, are provided. An example of this embodiment is an apparatus that includes a web address where the instructions can be viewed and/or from which the instructions can be downloaded. Conversely, means may be provided for obtaining the subject programming from a remote source, such as by providing a web address. Still further, the apparatus may be one in which both the instructions and software are obtained or downloaded from a remote source, as in the Internet or World Wide Web. Some form of access security or identification protocol may be used to limit access to those entitled to use the subject invention. As with the instructions, the means for obtaining the instructions and/or programming is generally recorded on a suitable recording medium.

Tailoring of Therapy

In one embodiment, the invention features use of the methods and compositions described herein in the context of tailoring therapy. Analysis of one or more risk factors for myocardial ischemia as described above can be used to provide information to the clinician as to the responsiveness of a patient to therapy. Assessment of platelet reactivity (particularly platelet aggregation) in tailoring anti-platelet therapy is of particular interest, and can be conducted in concert with assessment of one or more additional risk factors of a thrombotic risk profile and/or atherosclerotic risk profile as described above.

The invention can be used to aid selection of therapy and to assess and follow a selected therapy. Therapies for myocardial ischemic conditions include drug-based therapies (e.g., pharmacological or adjuvant therapies), mechanical therapies (e.g., surgical or non-surgical intervention associated with physical manipulation of tissue, e.g., stenting, angioplasty, grafting, and the like), or a combination or drug-based and mechanical therapy.

Of particular interest is assessment of efficacy (e.g., in reducing risk of thrombosis) of therapy involving administration of one or more anticoagulant or antithrombotic drugs. Anticoagulant drugs include reversible or irreversible anti-platelet inhibitors such as aspirin, glycoprotein IIb/IIIa (GP IIb/IIIa) inhibitors (e.g., abciximab (RePro™) (a chimeric monoclonal antibody), tirofiban (Aggrastat™, an RGD peptidomimetic), and eptifibatide (Integrelin™, a small peptide)), ADP-dependent aggregation inhibitors (e.g., clopidogrel, ticlopidine), and the like In particular, eptifibatide has demonstrated efficacy in the treatment of patients during coronary angioplasty, myocardial infarction and angina, and is indicated for administration in acute coronary syndromes (ACS) including acute myocardial infarction (AMI).

Anti-thrombotic drugs for which efficacy can be assessed, and therapy monitored, according to the invention include low molecular weight heparins (e.g., enoxaparin (Lovenox)), and direct antithrombotics such as hirudin, hirulog (bivaluridin), and argatroban.

Efficacy of mechanical intervention (including percutaneous or non-invasive interventions) can also be assessed using the methods and compositions of the invention. Examples of mechanical interventions include angioplasty, stenting (e.g., coronary stent), atherectomy, laser angioplasty, brachytherapy, percutaneous myocardial revascularization (PMR), intravascular ultrasound, and balloon valvuloplasty.

Efficacy of therapy can be assessed by examining improvement in one or more clinical symptoms of disease. Successful therapy is normally considered to be a significant improvement in one or more clinical symptoms after treatment.

An aspect of the invention of particular interest relates to assessing a patient's platelet reactivity (particularly by assessing platelet aggregation), assessing a patient's responsiveness to anti-platelet therapy, and tailoring therapy to suit a patient's platelet reactivity and/or responsiveness to anti-platelet therapy. As discussed above, the inventor has found that high platelet reactivity is associated with a high risk of an ischemic event, e.g., a thrombotic event, regardless of whether that platelet reactivity is responsive to therapy (e.g., regardless of whether platelet reactivity is reduced in response to administration of drug, e.g., an anti-platelet inhibitor such as clopidogrel).

Individual patients have variable response to anti-platelet medications. Furthermore, patients with low responsiveness to therapy (e.g., patients exhibiting drug resistance) may be at risk for complications (e.g., thrombosis). Moreover, this inter-individual variability in responsiveness to platelet inhibition has been clearly demonstrated in patients with atherosclerosis of the coronary arteries who have undergone coronary artery stenting. In these patients, it is desirable to give them anti-platelet medication to prevent thrombosis. The anti-platelet drug, clopidogrel (Plavix™) is most commonly used to prevent thrombosis in a standard amount.

As discussed herein, non-responder patients usually have high platelet reactivity and hence, greater risk of thrombosis.

Conversely, patients with low platelet reactivity have a small chance of thrombosis and seem to respond to even small amount of clopidogrel. Patients range from responsive, partially responsive, and non-responsive to clopidogrel therapy. In addition, another anti-platelet drug, aspirin, is associated with non-responsiveness.

According to the invention, patients with high platelet reactivity merit close monitoring and may require adjustment of anti-platelet regimen (e.g., adjustment of dose, dosing schedule, or drug). Alternatively, patients with low platelet reactivity need little or no medications. Tailoring therapy according to the invention thus avoids administration of drug to those patients who are at lower risk of complications (e.g., thrombosis) and/or allows the clinician to select a dosing regimen that avoids administration to an amount of drug that is greater than what is needed. In short, dose titration of drug can lead to a reduction in morbidity and mortality. Thus the invention helps reduce the incidence of side effects associated with drug-based therapy, as well as providing cost-savings.

Since most US adults take aspirin for cardiovascular prophylaxis, the implications are even more far-reaching. Indeed, stroke patients and patients with a tendency to suffer from blood clots (e.g., hypercoagulable state, coach class syndrome, women on birth control pills, patients with pulmonary embolism, etc.) would also benefit from such knowledge. Finally, in the peri-operative state where most patients are placed on anti-platelet therapy (intra-abdominal surgeries, orthopedic procedures, cardio thoracic operations, etc.); knowledge of platelet reactivity and hypercoaguability becomes very important in determining the need for and selection of therapy. Indeed, as more potent anti-platelet agents are developed, the ability to assess risk of thrombosis is of increased importance.

Newer and more powerful antiplatelet agents that target the same platelet receptor as clopidogrel are being developed. The ability to measure how an individual patient will respond to these medications in a reliable fashion is important. Undoubtedly, adjustment of these medications will reduce complications, enhance patient care and lead to cost-savings.

Treatment Regimen Modification

Modification of a treatment regimen includes one or more of: modifying (increasing or decreasing) the dosing frequency of the active agent administered; administering one or more additional active agents; modifying (increasing or decreasing) the amount of active agent administered; and administering a different active agent from the active agent, e.g., discontinuing administration of the active agent.

In some embodiments, modifying a dosing regimen comprises increasing the dosing frequency, e.g., increasing administering the active agent from once per week to twice per week, to three times per week, to daily, or to twice daily. Thus, e.g., in some embodiments, a method comprising administering an active agent at a frequency of once per week is modified such that the active agent is administered twice per week, three times per week, daily, or twice daily.

In some embodiments, modifying a dosing regimen comprises increasing the amount of active agent administered, e.g., increasing the amount of active agent administered over a given time period by at least about 25%, at least about 50%, at least about 100% or 2-fold, at least about 2.5-fold, at least about 3-fold, at least about 4-fold, or at least about 5-fold, or more. Thus, e.g., in some embodiments, a method comprising administering an active agent at a first dose over a given time period is modified such that the active agent is administered at a second dose that is at least about 25%, at least about 50%, at least about 100% or 2-fold, at least about 2.5-fold, at least about 3-fold, at least about 4-fold, or at least about 5-fold, or more, higher, over the same time period. As one non-limiting embodiment, where the active agent is administered at a dose of 100 µg TIW, and assessment of thrombotic risk indicates that this treatment regimen is not efficacious, the treatment regimen is modified to comprise administering 200 µg of the active agent TIW.

In some embodiments, a further risk assessment step is performed after the therapy modification step, to assess the efficacy of the modified treatment regimen. A further modification of the modified treatment regimen will in some embodiments be carried out.

In some embodiments, modifying a dosing regimen comprises administering at least a second active agent, and, in some embodiments comprises discontinuing administration of the first active agent. For example, in the context of anti-platelet therapy it may be desirable to administer two different types of anti-platelet drugs (e.g., an ADP-induced aggregation inhibitor (e.g., clopidogrel) and a GP IIa/IIIb inhibitor (e.g., eptifibatide)).

Kits

Kits including one or more of compositions for conducting an assay for a risk factor described herein, with reagents for a platelet aggregation assay. In addition to the compositions, the kits include an informational or instructional package insert describing the assay to be conducted and, in the case of a platelet aggregation assay, information relating to a risk threshold value for platelet aggregation, as described above. The instructions can be printed on a label affixed to the container, or can be a package insert that accompanies the container.

For example, the kit includes a chart to facilitate assessment of platelet aggregation and the associated risk of a thrombotic event. In another embodiment, the kit includes a scorecard for recording results of various assays to provide a "profile" or ThromboProfile™ of the patient's risk of thrombosis and/or atherosclerosis. In another embodiment, the kit includes a handheld device which is preprogrammed to receive one or more assay result values and/or to determine whether a platelet aggregation value is above or below a risk threshold value. The device can optionally provide a readout indicating an overall risk assessment and/or a risk assessment based on a platelet aggregation score.

Instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Study of Platelet Reactivity in Patients with and without Stent Thrombosis: Clopidogrel Resistance and Stent Thrombosis (CREST)

Methods and Materials

Patients and Blood Samples.

Cases of stent thrombosis (n=30) were identified by searching the medical records of patients who underwent coronary stenting in the last 1.5 years at the Sinai Hospital of Baltimore and Union Memorial Hospital, Baltimore, Md. This study was approved by the Investigational Review Board at the hospitals. Stent thrombosis was defined by the sudden onset of coronary artery occlusion in a stented vessel resulting in hospitalization and judged by the treating interventionalist as due to thrombosis. Platelet reactivity in patients with stent thrombosis (SAT) was compared to a group of patients without SAT. In patients without SAT, platelet studies were performed 5-14 days post-procedure and these patients were enrolled consecutively (n=100).

In patients with SAT, the average time from the occurrence of stent thrombosis to the initial blood drawn for laboratory evaluation was 218±204 days. In patients with SAT already receiving a maintenance dose of clopidogrel (75 mg·qd), blood was studied on the day of arrival at the Center. Those patients (n=2) not receiving clopidogrel at the time of the study were reloaded with 300 mg; maintained on 75 mg daily; and returned for blood draw 5 days later. Blood was drawn with a 21 g needle and placed into vacutainer blood collecting tubes (Becton—Dickinson, Rutherford, N.J.) containing 3.8% trisodium citrate after discarding the first 2-3 ml of free flowing blood. The vacutainer tube was filled to capacity and gently inverted 3 to 5 times to ensure complete mixing of the anticoagulant. Patients identified who were in-hospital had blood drawn at day 5 post-procedure. No patients in the study had been receiving Glycoprotein IIb/IIIa (GP IIb/IIIa) inhibitors or anticoagulants within 96 hours of blood sampling. All patients were receiving aspirin (81-325 mg qd) except two patients in SAT group.

Platelet Reactivity Measurements Platelet Aggregation.

Platelet aggregation was determined by conventional light transmittance aggregometry in response to 5 and 20 µM ADP (adenosine diphosphate); and 1.0 mM arachidonic acid using standard methods as previously described. Briefly, the blood citrate mixture was centrifuged at 120×g for 5 min to recover the platelet-rich plasma (PRP) and further subjected to centrifugation at 850×g for 10 min to recover platelet-poor plasma (PPP). The PRP and PPP were stored at room temperature for use within 2 h. The platelet count was determined in the PRPR sample and adjusted to $2-3\times10^8$/ml with homologous PPP. Platelets in PRP were stimulated with a final concentration of 5 and 20 µM ADP (Chronolog, Haverton, Pa.), and percent aggregation was assessed as previously described using a Chronolog Lumi aggregometer (Model 490A) with the Aggro-Link software package (Gurbel et al. J Am Coll Cardiol 1998 89:783).

GP IIb/IIa Receptors.

The surface expression of platelet receptors was determined by whole blood flow cytometry using a multicolor analysis method (Immunocytometry Systems, Cytometry Source Book, Becton Dickinson) with the following monoclonal antibodies: FITC (fluorescein isothiocyanate-conjugated) PAC-1 (recognizes the active GP IIb/IIIma receptor) and R-phycoerythrin (R-PE) conjugated CD41a (recognizes the total GP IIb/IIIa receptor population). Antibodies were obtained from BD Biosciences, San Diego, Calif. The blood-citrate mixture was stimulated with 5 µM ADP for 2 minutes. Saturating concentrations of respective antibodies were then added to unstimulated and simulated blood and the tubes were incubated at room temperature for 20 minutes in the dark. The labeled samples were fixed by the addition of 1% buffered paraformaldehyde and stored at 4° C. for at least 2 hours. The labeled samples were analyzed by a Becton Dickinson FACScan flow cytometer set up to measure fluorescence light scatter that was calibrated daily with fluorescence beads for the multicolor flow cytometer setup (CaliBRITE™3, BD Biosciences). After setting the gate around platelets, FL1(FITC)/FL2(R-PE) compensations were adjusted. All the variables were collected by use of 4-decade logarithmic amplification. The data were collected in list mode and then analyzed using CELL Quest Software (BD Biosciences). Total and activated GP IIb/IIIa receptor levels were expressed as log MFI (Gurbel et al. Thromb Res 2003; 112:9-12).

Vasodilator Stimulated Phosphoprotein (VASP).

The phosphorylation of VASP is a marker of $P2Y_{12}$ receptor reactivity and thus, clopidogrel-induced inhibition (Barragan et al. Catheter Cardiovasc Interv. 2003; 59:295-302). Stimulation of platelets by ADP leads to Gi-coupled inhibition of adenylate cyclase which, in turn reduces protein kinase activity and VASP phosphorylation levels. VASP phosphorylation levels were quantified with labeled monoclonal antibodies by flow cytometry using the Platelet VASP-$_{FCM}$ kit (Biocytex, Inc, Marseille, France). The $P2Y_{12}$ reactivity ratio is calculated after measuring the VASP phosphorylation levels following stimulation with $PGE_1$ (MFI $PGE_1$) and $PGE_1$+ADP (MFI $PGE_1$+ADP). The $P2Y_{12}$ reactivity ratio=[(MFI $PGE_1$)−(MFI $PGE_1$+ADP)/(MFI $PGE_1$)]×100%. Thus, the lower the ratio, the higher the clopidogrel induced inhibition of the $P2Y_{12}$ receptor.

Clopidogrel Resistance.

Clopidogrel resistance for purposes of this study was defined as $>75_{th}$ percentile for 5 and 20 µM ADP-induced aggregation as measured in the group without SAT. Aspirin resistance was defined as >14% change in light transmittance after stimulation with arachidonic acid (Gum et al. J Am Coll Cardiol. 2003; 4:961-5).

Statistical Analysis.

Comparisons were made between groups by one way analysis of variance (Statistica software, Tulsa, Okla.). Standard regression analysis was used to correlate aggregation with the other markers measured. (Statistica software, Tulsa, Okla.). The Wilks-Shapiro test was used to assess conformity with a normal distribution. Based on the normal distribution of data, the mean±SD and mean±SE were used and P<0.05 was considered significant.

Results

Patients.

A total of 5355 interventional coronary procedures were performed at the 2 hospitals over an 18 month period and thirty patients (0.6%) were identified as having SAT. Among these patients, there were 3 deaths; 5 patients could not be contacted; 2 did not participate because of clopidogrel allergy (skin rash); and the remaining twenty patients agreed to participate in the study. Among these 20 patients, 18 were receiving a 75 mg maintenance dose of clopidogrel and 2 patients were retreated with clopidogrel. 18/20 SAT patients were on aspirin therapy (81-325 mg per day). The mean time to SAT (time from the day of procedure to the development of SAT) was 23±16 days.

Demographics.

The clinical and angiographic characteristics of both groups are shown in Tables 1 and 2, respectively. All of the non-SAT interventions were performed electively whereas 12 (60%) of procedures resulting in SAT were performed emergently. The ages of both groups were the same. Patients with SAT had a non-significantly greater incidence of family history of CAD. Hematological data did not differ between groups. The ejection fraction was lower and the total lesion length was greater in the SAT group.

TABLE 1

Patient Demographics

|  | SAT (n = 20) | No SAT (n = 50) | p-value |
|---|---|---|---|
| Age (years) | 65 ± 11 | 62 ± 13 | NS |
| Race (Caucasian) n, (%) | 10 (50) | 38 (76) | .04 |
| Gender (Male) n, (%) | 10 (50) | 35 (70) | NS |
| Risk Factors/Past medical Hx n, (%) |  |  |  |
| Smoking | 9 (45) | 27 (54) | NS |
| Family history of CAD | 16 (80) | 28 (56) | .06 |
| Hypertension | 15 (75) | 28 (56) | NS |
| Hyperlipidemia | 15 (75) | 36 (77) | NS |
| Diabetes | 12 (60) | 21 (42) | NS |
| Prior Myocardial Infarction | 12 (60) | 24 (48) | NS |
| Prior CABG | 5 (25) | 12 (24) | NS |
| Prior PTCA | 4 (20) | 20 (40) | NS |
| Baseline Medications n, (%) |  |  |  |
| Beta blockers | 17 (85) | 45 (90) | NS |
| ACE Inhibitors | 15 (75) | 26 (52) | NS |
| Calcium blockers | 5 (25) | 10 (20) | NS |
| Lipid lowering agents |  |  |  |
| 3A4 | 11 (55) | 29 (58) | NS |
| Non 3A4 | 5 (25) | 13 (26) | NS |

CABG = coronary artery bypass graft surgery;
CAD = coronary artery disease;
PTCA = percutaneous coronary angioplasty;
ACE = angiotensin converting enzyme;
SAT = stent thrombosis

TABLE 2

Procedural Characteristics

|  | SAT (n = 20) | No SAT (n = 50) | p Value |
|---|---|---|---|
| Ejection Fraction (%) | 40 ± 10 | 53 ± 6 | .001 |
| Number of vessels treated | 1.3 ± 0.4 | 1.4 ± 0.7 | NS |
| Lesion Morphology |  |  |  |
| Denovo n, (%) | 20 (100) | 46 (92) | NS |
| Lesion Location n, (%) |  |  |  |
| LAD | 5 (30) | 14 (28) | NS |
| CX | 3 (15) | 11 (22) | NS |
| RCA | 12 (60) | 17 (34) | .05 |
| SVG | 0 (0) | 8 (16) | NS |

TABLE 2-continued

Procedural Characteristics

|  | SAT (n = 20) | No SAT (n = 50) | p Value |
|---|---|---|---|
| Stent Types |  |  |  |
| Drug eluting n, (%) | 6 (30) | 31 (62) | .01 |
| Bare metal n, (%) | 14 (70) | 16 (32) | .01 |
| Reference vessel diameter (mm) | 2.8 ± 0.3 | 3.1 ± 0.4 | NS |
| Total lesion length (mm) | 24 ± 6 | 18 ± 8 | .007 |
| Pre-stenosis (%) | 94 ± 7 | 87 ± 12 | NS |
| Post-stenosis (%) | 9 ± 12 | 3 ± 6 | NS |

CX = circumflex artery;
LAD = left anterior descending artery;
RCA = right coronary artery;
SVG = saphenous vein graft Platelet Data.

Platelet aggregation in response to 5 and 20 µM ADP was higher in the group with SAT as compared to the group without SAT (FIGS. 1 and 2, p<0.05 for both 5 µM and 20 µM ADP-induced aggregation). Patients with SAT had greater active GP IIb/IIIa expression and a higher $P2Y_{12}$ reactivity ratio whereas total GP IIb/IIIa expression was not significantly different between groups (Table 3). CD41, which is a measure of total receptor expression, served as a control.

TABLE 3

Platelet Characteristics

|  | No SAT | SAT | p Value |
|---|---|---|---|
| LTA - 5 µM ADP (%) | 26 ± 2 | 49 ± 4 | <0.001 |
| LTA - 20 µM ADP (%) | 46 ± 2 | 65 ± 3 | <0.001 |
| LTA - Arachidonic Acid | 0 non-responder | 1 non-responder | NS |
| $P2Y_{12}$ Reactivity Ratio | 46 ± 9 | 69 ± 5 | 0.030 |
| GP IIb/IIIa (MFI) |  |  |  |
| Unstimulated | 15 ± 3 | 9 ± 1 | NS |
| Stimulated | 42 ± 4 | 138 ± 19 | <0.001 |
| CD 41 (MFI) |  |  |  |
| Unstimulated | 513 ± 30 | 515 ± 31 | NS |
| Stimulated | 729 ± 60 | 770 ± 38 | NS |

LTA = light transmittance aggregometry;
MFI = mean fluorescence intensity;
NS = not significant The estimated incidence of clopidogrel resistance was 65% and 60% as measured by 5 µM and 20 µM ADP-induced aggregation, respectively (FIGS. 1 and 2). The r value comparing 5 µM ADP-induced aggregation to 20 M ADP-induced aggregation was 0.93. The reactivity ratio by VASP assay correlated strongly with 20 µM ADP-induced aggregation (r=0.57). The correlation of stimulated active GP IIb/IIIa expression with aggregation was weaker (r=0.36 with 5 µM ADP-induced aggregation and 0.29 with 20 µM ADP-induced aggregation, respectively). All patients were responsive to aspirin except 1 in the SAT group (54% aggregation). Arachidonic acid induced aggregation (1 mM) was 4±2% in the non-SAT group vs. 3±2% in the SAT group (p=NS).

The findings above demonstrate a strong association between heightened platelet reactivity, particularly as detected by platelet aggregation, low responsiveness to clopidogrel, and the development of stent thrombosis.

Based on these data, platelet aggregation below about 40% for 20 µM ADP is associated with a 0% incidence of SAT. Importantly, the data from this study indicate that platelet reactivity alone, particularly as measured by ADP-induced platelet aggregation, is a predictor of risk of SAT. Platelet aggregation in patients without SAT was assessed at 5-14 days post-procedure (e.g., post-stent). Of those who experienced SAT the average time from this initial blood draw to occurrence of stent thrombosis was 218±204 days, or from about 6 months to about 14 months.

The 0.6% incidence of SAT in this study is in agreement with previously reported data indicating the incidence of subacute stent thrombosis to be in the range of 0.4% to 3% in high risk patients, with an incidence of 0.4% in 500 patients treated with a sirolimus-eluting stent (Reynolds et al. J Invasive Cardiol. 2002; 14:364-8; Regar et al. Am J Cardiol. 2004; 93:1271-5). Most of the patients with SAT in this study had their index procedure performed emergently and had long lesions. These risk factors are also supported by other studies (Reynolds et al. J Invasive Cardiol. 2002; 14:364-8; Regar et al. Am J Cardiol. 2004; 93:1271-5).

The results above illustrates that the variability in final platelet reactivity in a patient given the standard dose of clopidogrel. In the present study, platelet aggregation was measured using two agonist concentrations. There was a strong correlation between aggregation induced by both agonist concentrations. In addition, platelet receptor expression was significantly greater in the SAT group. These results demonstrate that irrespective of the methodology chosen to measure platelet reactivity (e.g., light transmittance aggregometry, active GP IIb/IIIa, or VASP-phosphorylation levels, or thromboelastography), the response to clopidogrel therapy is indeed heterogeneous, and patients with stent thrombosis have greater platelet reactivity to ADP than patients without stent thrombosis.

The VASP assay is a direct measure of $P2Y_{12}$ reactivity and therefore directly assesses the intrinsic functional response of the receptor in the presence of clopidogrel. The results above strongly suggest that the $P2Y_{12}$ receptor is not adequately inhibited in a large percentage of patients who have experienced SAT.

Clopidogrel resistance has been previously defined as less than 10% absolute change in aggregation compared to a pre-treatment baseline (Gurbel et al. Circulation. 2003; 107:2908-13). In contrast, the study presented herein a baseline measurement of platelet reactivity was not determined, as this study was not prospective with respect to the SAT group. Given the overall low event rate of SAT, the number of patients required to assess the relation of platelet reactivity to SAT in a prospective investigation was prohibitively large. Therefore, clopidogrel resistance was defined as a response higher than the $>75_{th}$ percentile measurement with the respective marker in the patients without SAT.

Although there is no uniformity in the definition of aspirin resistance, various measurements of platelet function in patients receiving aspirin have been correlated to a greater risk of cardiovascular events. The prevalence of aspirin resistance has been reported between 5-45% (Mason et al. Rev Cardiovasc Med. 2004; 5; 156-163; Eikelboom et al. Circulation. 2002; 105:1650-5; Zimmermann et al. Circulation. 2003; 108:542-7). Of interest, in the present study platelet reactivity was very low in response to 1.0 mM arachidonic acid. These results are discordant with observations by other investigators (Gum et al. J Am Coll Cardiol. 2003, 4:961-5; Eikelboom et al. Circulation. 2002; 105:1650-5). Gum et al estimated aspirin resistance by using a combination of responsiveness to both ADP and a slightly higher dose of arachidonic acid (1.6 mM). In their study mean aggregation in response to arachidonic acid was 11.4±10.3% as compared to ~4% in the present study. The lower arachidonic acid concentration in the present study may in part explain why only 1/70 (1.5%) met the criteria for resistance as compared 5.5% in the Gum et al. study. The effect of aspirin to block cyclooxygenase activity is likely much more uniform whereas the effect on platelet aggregation as measured by agonists other than arachidonic acid is influenced by many factors. Therefore, aspirin resistance secondary to a lack of inhibition of cyclooxygenase is probably rare as reflected in the present study.

Limitations.

Platelet studies were performed at different times in non-SAT and SAT patients. Non-SAT patients were enrolled and studied prospectively whereas patients with SAT were identified retrospectively and subsequently studied. The analyses of platelet reactivity conducted at different intervals from the index procedure may affect the results. However, it has been previously demonstrated that clopidogrel responsiveness is lowest early after stenting (Gurbel et al. Circulation. 2003; 107:2908-13). Therefore, this fact would only strengthen the discovery here, since at a later date it would be expected that the non-SAT patients would have even higher clopidogrel responsiveness. In conclusion, the current study indicates that high platelet reactivity and low clopidogrel responsiveness are risk factors for SAT.

Example 2

Clopidogrel Loading with Eptifibatide to Arrest the Reactivity of Platelets

Methods

This study was approved by the Investigational Review Board. Consecutive patients undergoing elective coronary stenting were enrolled after giving informed consent. Patients were >18 years old. The exclusion criteria were: a history of bleeding diathesis, acute myocardial infarction within 48 hours, elevated cardiac markers (above upper limits normal for the respective assay), cerebrovascular event within 3 months, chronic vessel occlusion or angiographically visible thrombus, illicit drug or alcohol abuse, prothrombin time greater than 1.5 times control, platelet count <100,000/$mm^3$, hematocrit <30%, creatinine >4.0 mg/dl, and thienopyridine or glycoprotein (GP) IIb/IIIa use prior to the procedure.

Patients were randomly assigned to one of four treatment regimens by a computer generated assignment that was chosen from a sealed envelope by the study personnel: Group A) clopidogrel (300 mg); Group B) clopidogrel (600 mg); Group C) clopidogrel (300 mg+eptifibatide); and Group D) clopidogrel (600 mg)+eptifibatide. The clopidogrel loading dose was given to all patients immediately after stenting and was followed by 75 mg daily. In addition, all patients had received at least 81 mg aspirin for 7 days prior to the procedure (>90% received 325 mg) and 325 mg was administered on the day of the procedure and daily thereafter. Eptifibatide was administered using the ESPRIT study protocol as a double bolus (180 µg/kg) followed by an infusion (2 µg/kg/min) for 18-24 hours post procedure. Unfractionated heparin was administered according to the ESPRIT dosing regimen (60 U/kg) as a bolus to all patients in the catheterization laboratory immediately prior to stenting.

Blood Sampling.

Baseline blood samples were obtained in the catheterization laboratory through the indwelling femoral vessel sheath and transferred to vacutainer blood collecting tubes (Becton—Dickinson, Rutherford, N.J.) containing 3.8% trisodium citrate after discarding the first 2-3 ml of free flowing blood. The vacutainer tube was filled to capacity and gently inverted 3 to 5 times to ensure complete mixing of the anticoagulant. Samples were obtained before clopidogrel, eptifibatide and heparin administration (baseline); and at 3 hours, 8 hours, and 18-24 hours post-stenting. The 18-24 hour blood draw was performed at the time of completion of the eptifibatide infusion.

Platelet Aggregation.

The blood-citrate tubes were centrifuged at 120 g for 5 minutes to recover platelet rich plasma (PRP) and further centrifuged at 850 g for 10 minutes to recover platelet poor plasma (PPP). The platelet count was determined in the PRP sample and adjusted to $3.0 \times 10^8$/ml with homologous platelet poor plasma. The PRP and PPP were stored at room temperature to be used within two hours. Platelet aggregation was assessed as described previously. Briefly, platelets were stimulated with 5 and 20 μM ADP and the aggregation was assessed using a Chronolog Lumi-Aggregometer (Model 490-4D) with the aggregolink software package (Chronolog, Havertown, Pa.). Aggregation was expressed as the maximum percent change in light transmittance from baseline, using PPP as a reference.

Whole Blood Flow Cytometry.

The surface expression of platelet receptors was determined by whole blood flow cytometry using three-color analysis method (Immunocytometry Systems, Cytometry Source Book, Becton Dickinson) with the following monoclonal antibodies: FITCconjugated PAC-1 (recognizes activated GP IIb/IIIa receptors), R-Phycoerythrin (R-PE)-conjugated CD41a (recognizes total GP IIb/IIIa receptors), and CY-Chrome™ conjugated CD62P (recognizes p-selectin). All three antibodies were purchased from BD Biosciences, San Diego, Calif. The blood-citrate mixture was stimulated with 5 μM ADP for 2 minutes. Saturating concentrations of respective antibodies were then added and the tubes were incubated at room temperature for 20 minutes in the dark. The labeled samples were fixed by the addition of 1% buffered paraformaldehyde and stored at 4° C. for at least 2 hours. The labeled samples were analyzed by a Becton Dickinson FACScan flow cytometer set up to measure fluorescence light scatter. The instrument was calibrated with fluorescence beads for the three-color flow cytometer setup (CaliBRITE™ 3, BD Biosciences). After setting the gate around platelets, FL1 (FITC)/FL2 (R-PE) and FL2 (R-PE)/FL3 (CY-Chrome™) compensations were adjusted. All the variables were collected by use of 4-decade logarithmic amplification. The data were collected in list mode and then analyzed using CELL Quest Software (BD Biosciences). P-selectin was expressed as percent positive cells (i.e. the ratio of CD62P (CY-Chrome™) verses CD41a (R-PE) positive cells) as previously described. Activated GP IIb/IIIa was expressed as log mean fluorescence intensity.

Myocardial Necrosis Markers.

Cardiac markers were measured at the same times as the platelet assays. The peak levels of troponin I, creatinine kinase MB (CKMB), and myoglobin were determined using the Triage® Cardiac Panel with a Triage® Meter (Biosite Inc., San Diego, Calif.). This method is based on a fluorescence immunoassay for the quantitative determination of these cardiac markers. The upper limit of normal (ULN) value for troponin I is 1.0 ng/ml; for myoglobin is 107 ng/ml; and for CKMB is 4.3 ng/ml.

Definitions.

Relative platelet inhibition was defined for purposes of this study as follows: (baseline aggregation minus posttreatment aggregation)/baseline aggregation×100%.[14] Mean platelet reactivity was calculated as the average platelet aggregation recorded at 3, 8 and 18-24 hours poststenting. Relative inhibition of active GP IIb/IIIa expression was defined as follows: (baseline MFI minus post-treatment MFI/baseline MFI). The definition of an infarct was CK-MB>3× upper limits normal (ULN) in at least 2 samples and a large infarct was defined as CK-MB>5×ULN in at least 2 samples.[10,13] Bleeding was quantified according to the TIMI criteria.[16] In brief, major bleeding was defined as clinically overt bleeding accompanied by a fall in hemoglobin of 3.0-5.0 g/dl or a fall in hematocrit of 9 to <15%. Major bleeding occurred when the hemoglobin decreased >5 g/dl or the hematocrit ≥15%.

Sample Size and Statistical Analysis.

Previous studies had shown that a 300 mg clopidogrel loading dose produces <40% inhibition of baseline aggregation in response to 5 and 20 μM ADP at 24 hours after administration. Other studies demonstrated >80% inhibition by eptifibatide. Using the statistical calculation m=2× $[Z_{(1-\acute{a}/2)} + Z_{(1-\hat{a})}]_{2/0.2}$, where m=number of patients, statistical significance level (α)=5%, power (β)=90% and Δ=standardized difference; approximately 30 patients will be needed in each arm in the study. Comparisons were made between groups by one way analysis of variance (Statistica software, Tulsa, Okla.). The Wilks-Shapiro test was used to assess conformity with a normal distribution. Based on the normal distribution of data the mean±SEM is reported except as otherwise noted and p<0.05 was considered significant.

Results

Patients.

One hundred and twenty patients were enrolled and had platelet assays performed. The clinical and angiographic demographics of the four treatment groups are shown in Tables 4 and 5, respectively.

TABLE 4

Patient Demographics

| | Group A (n = 30) | Group B (n = 30) | Group C (n = 30) | Group D (n = 30) |
|---|---|---|---|---|
| Age (years) | 68 ± 21 | 55 ± 30 | 58 ± 12 | 64 ± 9 |
| Race (Caucasian) n, (%) | 20 (67) | 26 (87) | 25 (84) | 19 (64) |
| Gender (Male) n, (%) | 13 (43) | 19 (63) | 22 (73) | 18 (60) |
| Risk Factors/Past medical Hx n, (%) | | | | |
| Smoking | 20 (67) | 19 (64) | 14 (46) | 21 (70) |
| Family history of CAD | 16 (53) | 18 (60) | 9 (30) | 21 (70) |
| Hypertension | 21 (70) | 20 (67) | 20 (67)) | 27 (90) |
| Hyperlipidemia | 21 (70) | 24 (77) | 26 (87) | 26 (87) |
| Diabetes | 16 (53) | 9 (30) | 12 (40) | 11 (37) |
| Prior Myocardial Infarction | 7 (23) | 10 (33) | 8 (27) | 8 (27) |
| Prior CABG | 5 (17) | 5 (17) | 6 (20) | 3 (9) |
| Prior PTCA | 13 (43) | 9 (30) | 13 (43) | 8 (27) |
| Pretreatment Medications n, (%) | | | | |
| Beta blockers | 27 (90) | 25 (84) | 27 (90) | 29 (97) |
| ACE Inhibitors | 20 (67) | 19 (64) | 23 (77) | 24 (80) |
| Calcium blockers | 5 (17) | 7 (23) | 3 (9) | 5 (17) |
| Lipid lowering agents | | | | |
| 3A4 Pathway metabolized | 16 (53) | 16 (53) | 21 (70) | 11 (37) |
| Non 3A4 Pathway metabolized | 7 (24) | 6 (20) | 6 (20) | 10 (33) |
| Laboratory Data | | | | |
| WBC (×1000/mm³) | 8.2 ± 3.8 | 8.3 ± 3.6 | 7.9 ± 2.5 | 7.2 ± 1.8 |
| Platelets (×1000/mm³) | 250 ± 106 | 230 ± 90 | 232 ± 71 | 204 ± 34 |
| Hemoglobin (g/dl) | 12.4 ± 2.0 | 12.9 ± 1.8 | 13.7 ± 1.7 | 12.7 ± 2.0 |
| Creatinine (g/dl) | 1.2 ± 1.1 | 1.15 ± 0.4 | 0.89 ± 0.2 | 1.0 ± 0.2 |

Data Reported as Mean ± SD
ACE = angiotensin converting enzyme;
CABG = coronary artery bypass graft surgery;
CAD = coronary artery disease;
PTCA = percutaneous coronary angioplasty;
WBC = white blood cells

TABLE 5

Procedural Characteristics

|  | Group A (n = 30) | Group B (n = 30) | Group C (n = 30) | Group D (n = 30) |
| --- | --- | --- | --- | --- |
| Length of procedure (min.) | 72 ± 38 | 62 ± 19 | 67 ± 37 | 54 ± 17 |
| Ejection Fraction (%) | 53 ± 8 | 55 ± 8 | 49 ± 11 | 53 ± 9 |
| Number of vessels treated | 1.3 ± 0.5 | 1.3 ± 0.6 | 1.4 ± 0.6 | 1.5 ± 0.7 |
| Lesion Morphology |  |  |  |  |
| Denovo n, (%) | 29 (97) | 26 (87) | 26 (87) | 27 (90) |
| Lesion Location n, (%) |  |  |  |  |
| LAD | 10 (33) | 9 (30) | 13 (43) | 9 (30) |
| CX | 4 (13) | 9 (30) | 9 (30) | 8 (27) |
| RCA | 14 (47) | 11 (37) | 5 (17) | 12 (40) |
| SVG | 2 (7) | 1 (3) | 3 (10) | 1 (3) |
| Stent Types n, (%) |  |  |  |  |
| Drug eluting | 16 (53) | 22 (73) | 18 (60) | 20 (67) |
| Bare metal | 12 (40) | 6 (20) | 9 (30) | 9 (30) |
| PTCA only | 2 (7) | 2 (7) | 3 (10) | 1 (3) |
| Reference vessel diameter (mm) | 2.9 ± 0.5 | 3.2 ± 0.5 | 3 ± 0.4 | 3 ± 0.4 |
| Total lesion length (mm) | 18.5 ± 10 | 22.5 ± 15 | 22 ± 15 | 20 ± 12 |
| Pre-stenosis (%) | 81 ± 8 | 85 ± 6 | 88 ± 5 | 83 ± 7 |
| Post-stenosis (%) | 2 ± 0.5 | 4 ± 2 | 5 ± 3 | 4 ± 2 |
| Procedural success n, (%) | 30 (100) | 28 (93) | 29 (97) | 28 (93) |

Data Reported as Mean ± SD
CX = circumflex artery;
LAD = left anterior descending artery;
RCA = right coronary artery;
SVG = saphenous vein graft Group A was the oldest and Group C had the highest percentage of males. Cardiovascular risk factors were common and the incidence of diabetes was high in all groups. One patient in each group had presented with a non-ST elevation myocardial infarction. The use of statins metabolized by the CYP 3A4 pathway was the lowest in Group D. Concomitant medications were frequently used in all groups. Multivessel interventions were commonly performed and drug-eluting stents were often used. There were no in-hospital deaths. There was one ST-elevation myocardial infarction that occurred in-hospital following a subacute thrombosis in a patient assigned to Group A.

There were no strokes or episodes of congestive heart failure. Hematomas were the cause of all bleeding episodes. Minor bleeding occurred in one patient in Group A and major bleeding occurred in 1 patient each in Groups C and D.

Platelet Aggregation.

Figure 4:
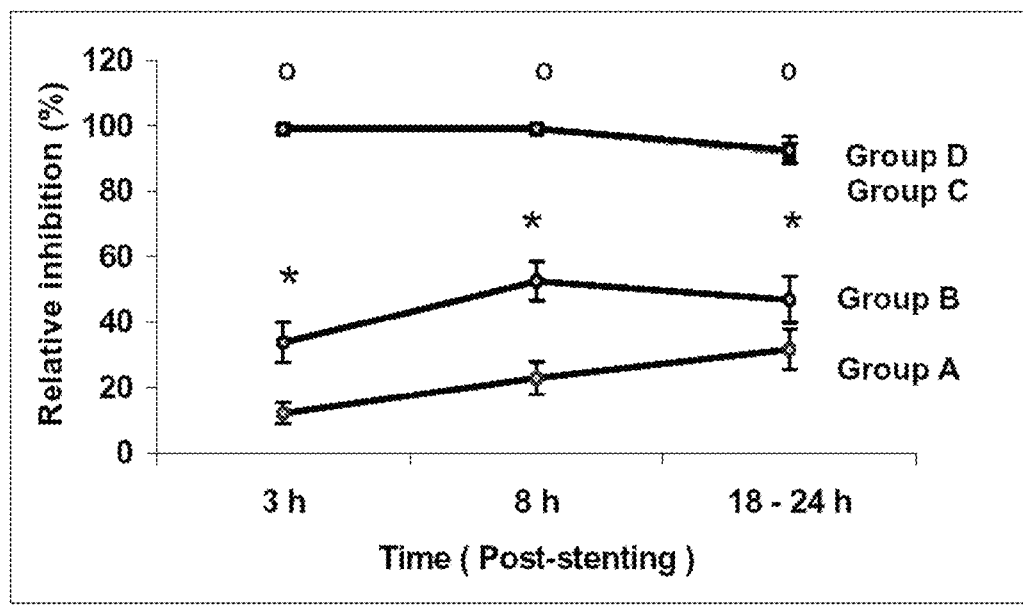
FIG. 4 is a graph showing platelet inhibition in response to 5 M ADP following the 4 treatment regimens. Group A=300 mg clopidogrel; Group B=600 mg clopidogrel; Group C=300 mg clopidogrel+eptifibatide; and Group D=300 mg clopidogrel+eptifibatide. * p≤0.001, Group A vs. B; o p<0.001, Groups C or D vs. Groups A or B.

FIG. 4 shows the pharmacodynamic responses in the four groups in response to 5 μM ADP. In the groups not treated with eptifibatide, baseline aggregation was 63±11% in Group A and 66±7% in Group B (p=NS). In the groups treated with eptifibatide, baseline aggregation was 58±11% in Group C and 62±7% in Group D (p=NS). In the groups not treated with eptifibatide, a 600 mg clopidogrel loading dose provided greater platelet inhibition throughout the first 24 hours after stenting. Group B had greater inhibition than Group A at 3 hours (p<0.001); 8 hours (p<0.001); and 18-24 hours (p<0.001). The peak inhibitory effect following a 600 mg loading dose occurred at 8 hours as compared to 18-24 hours following a 300 mg loading dose. Groups C and D exhibited the same inhibition (p=NS at all times) and both groups exhibited 2 twofold greater inhibition as compared to Groups A and B at all times (p<0.001).

Figure 5:
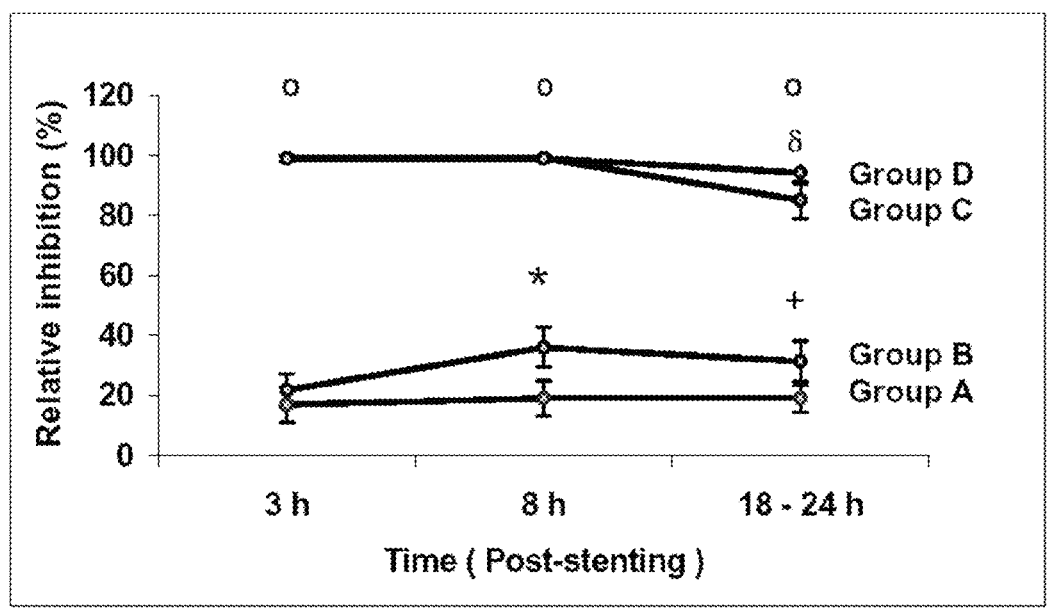
FIG. 5 is a graph showing platelet inhibition in response to 20 µM ADP following the 4 treatment regimens. Group A=300 mg clopidogrel; Group B=600 mg clopidogrel; Group C=300 mg clopidogrel+eptifibatide; and Group D=300 mg clopidogrel+eptifibatide. * p=0.001, Group A vs. B.+p=0.01, Group A vs. B. o p<0.001, Groups C and D vs. Groups A and B δ p=0.05, Group C vs. D.

FIG. 5 shows the platelet response to 20 μM ADP. Baseline aggregation did not differ between groups. The groups receiving clopidogrel and eptifibatide had consistently the lowest reactivity over 24 hours (p<0.001 vs. Groups A and B at all times). At a 20 μM agonist concentration Group D showed greater inhibition at 18-24 hours as compared to Group C (p=0.05). Group B had the same inhibition as Group A at 3 hours (p=0.55); and greater inhibition at 8 hours (p=0.09); and 18-24 hours (p=0.01). The peak inhibitory effect following a 300 or 600 mg loading dose was reached at 8 hours.

Flow Cytometry.

Figure 6:
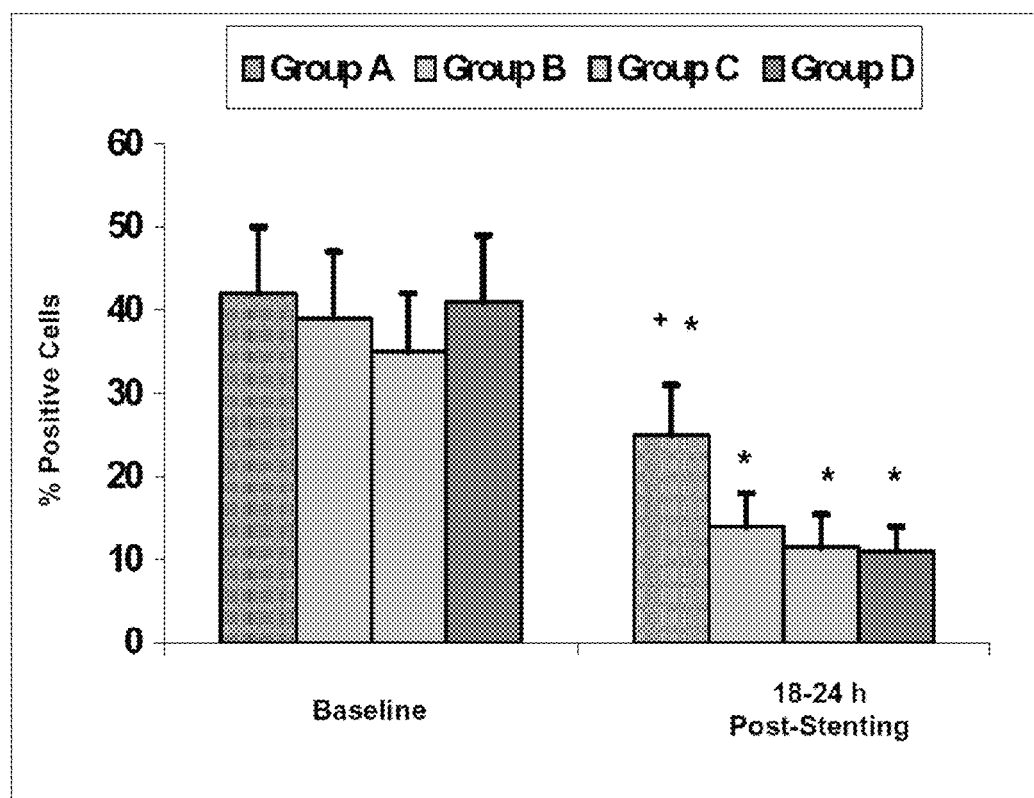
FIG. 6 is a graph showing stimulated p-selectin expression at baseline and 18-24 hours post-stenting. * p≤0.02 vs. baseline; +p≤. 0.03 vs. Groups B, C, or D. Group A=300 mg clopidogrel; Group B=600 mg clopidogrel; Group C=300 mg clopidogrel+eptifibatide; and Group D=300 mg clopidogrel+eptifibatide.
Figure 7:
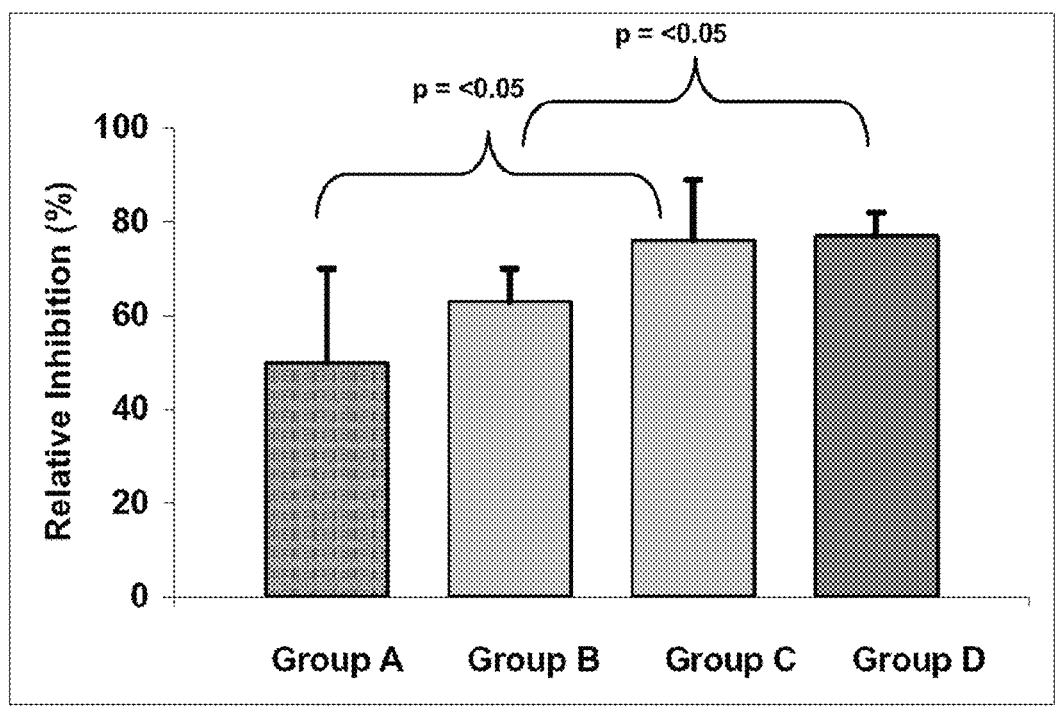
FIG. 7 is a graph showing relative inhibition of active GP IIb/IIIa expression at 18-24 hours post-stenting. Group A=300 mg clopidogrel; Group B=600 mg clopidogrel; Group C=300 mg clopidogrel+eptifibatide; and Group D=300 mg clopidogrel+eptifibatide.

Stimulated p-selectin expression at baseline did not differ between groups. Post-treatment p-selectin expression was significantly reduced in all groups as compared to baseline expression whereas treatment with 300 mg clopidogrel alone had the least effect in p-selectin expression (FIG. 6). Stimulated expression of active GP IIb/IIIa measured at 18-24 hours was inhibited the most in Groups C (76±13%) and D (77±5%) as compared to Groups A (50±20%, p<0.05) and B (63±7%, p<0.05) (FIG. 7).

Myocardial Necrosis Markers.

Figure 8:
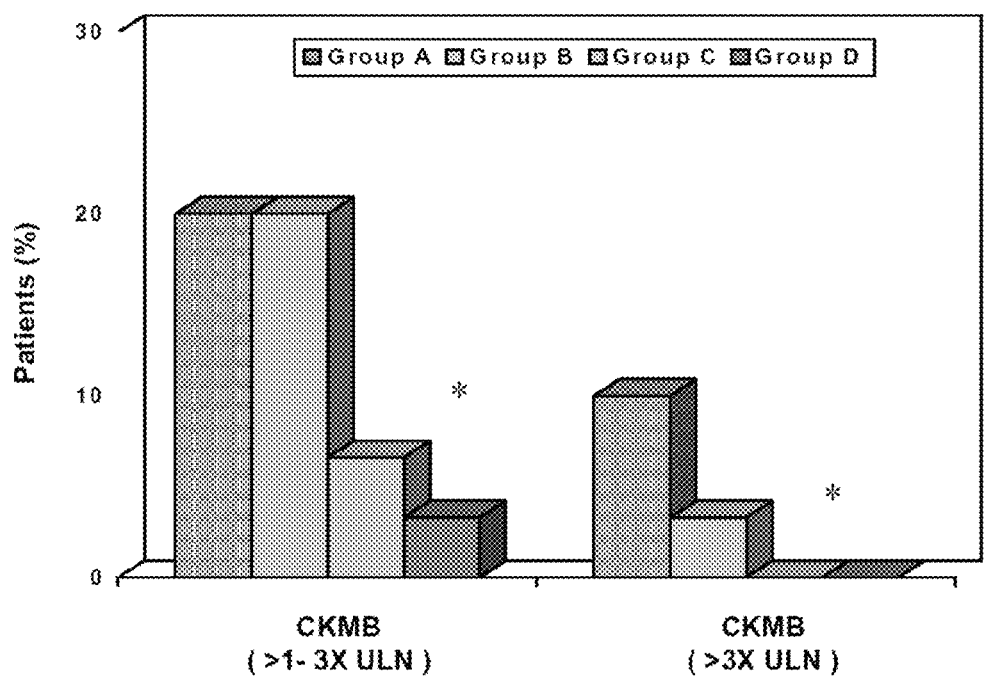
FIG. 8 is a bar graph demonstrating CK-MB release in the 4 treatment groups. * p<0.05 between groups C and D vs. A and B. Group A=300 mg clopidogrel; Group B=600 mg clopidogrel; Group C=300 mg clopidogrel+eptifibatide; and Group D=300 mg clopidogrel+eptifibatide. ULN=upper limit of normal value.

Overall, CKMB release (>1-3×ULN) was lowest in the groups treated with eptifibatide (p<0.005) (FIG. 8 and Table 6).

TABLE 6

Necrosis Markers

| Markers | Group A (n = 30) | Group B (n = 30) | Group C (n = 30) | Group D (n = 30) |
| --- | --- | --- | --- | --- |
| CKMB (>1-3X ULN) (n) | 6 | 6 | 2 | 1 |
| CKMB (>3X ULN) (n) | 3 | 1 | 0 | 0 |
| TN-1 (>ULN) (n) | 7 | 4 | 2 | 1 |
| Myoglobin (>2X ULN) (n) | 7 | 6 | 3 | 0 |

TN = troponin

Figure 9:
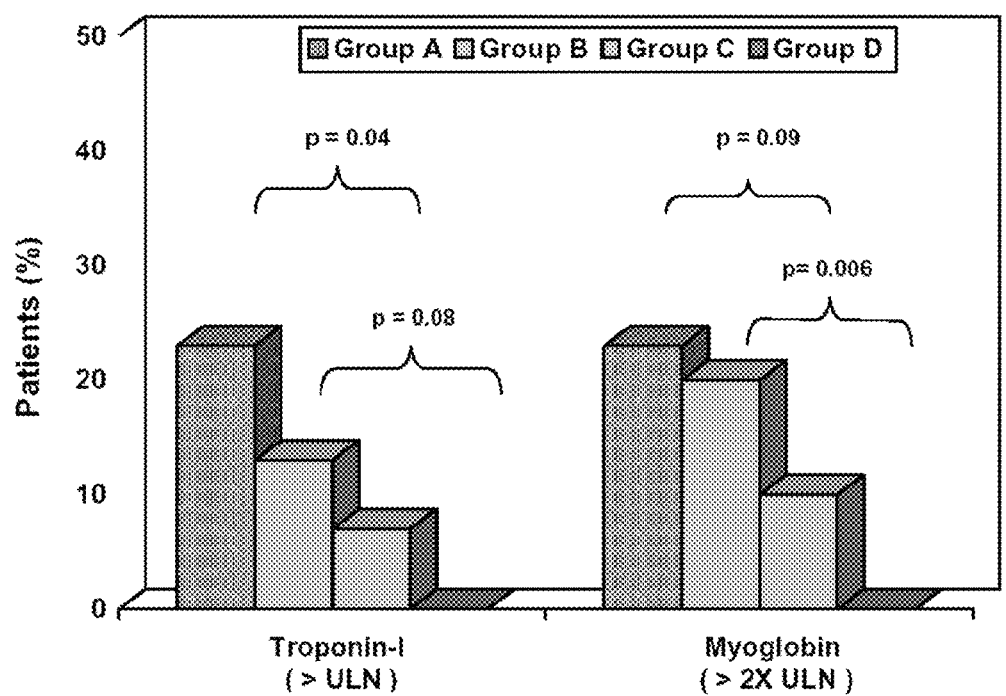
FIG. 9 is a bar graph demonstrating myoglobin and troponin release in the 4 treatment groups. Group A=300 mg clopidogrel; Group B=600 mg clopidogrel; Group C=300 mg clopidogrel+eptifibatide; and Group D=300 mg clopidogrel+eptifibatide. ULN=upper limit of normal value.

Criteria were met for a myocardial infarction in 3 patients from Group A and 1 from group B (p<0.03 for eptifibatide vs. clopidogrel alone). There were no large infarcts in either group that received eptifibatide whereas 2 occurred in Group A and 1 in Group B. Similar findings were observed when troponin and myoglobin were measured (FIG. 9). A trend to less troponin elevation was observed in Group B as compared to Group A (p=0.10). Inhibition of either troponin I or myoglobin release was lower in patients treated with eptifibatide+clopidogrel compared to clopidogrel alone (p=0.004 and p=0.002, respectively) (FIG. 9).

Relation of Platelet Reactivity to Myocardial Necrosis.

Figure 10:
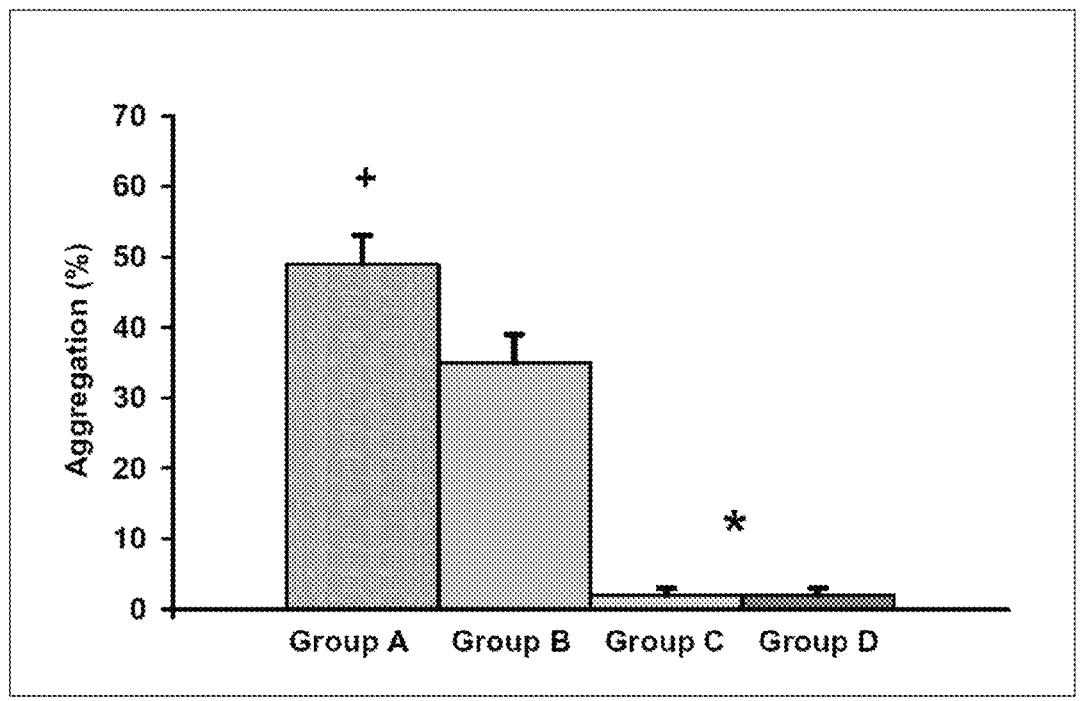
FIG. 10 is a bar graph demonstrating mean platelet reactivity measured over 18-24 hours post-stenting by 5 µM ADP-induced aggregation.+p=0.002 between groups A and B, * p<0.001 between either Group C or D vs. Group A or B. Group A=300 mg clopidogrel; Group B=600 mg clopidogrel; Group C=300 mg clopidogrel+eptifibatide; and Group D=300 mg clopidogrel+eptifibatide.

FIG. 10 demonstrates that eptifibatide use was associated with the lowest mean platelet reactivity and 300 mg clopidogrel alone was associated with higher mean platelet reactivity than 600 mg clopidogrel alone. FIG. 11 demonstrates the overall relation of myocardial necrosis marker release to mean platelet reactivity. Mean platelet reactivity was significantly higher in those patients who developed a myocardial infarction or any increased myocardial marker release. Myocardial infarction only occurred in those patients with mean 5 μM ADP-induced aggregation greater than about 50% (FIG. 12). FIG. 12 demonstrates that mean 20 μM ADP-induced aggregation was also correlated with myocardial infarction.

The current study demonstrates that the incremental increases in cardiac marker release observed in patients with higher levels of post-treatment platelet reactivity lend strong support to the concept that reactive platelets play a central role in the mediation of post-stent myocardial necrosis. The absence of infarcts in patients with lower than about 50% mean 5 μM ADP-induced aggregation indicates a threshold effect. Thus a 5 μM ADP-induced platelet aggregation score of less than 50%, regardless of the percent reduction relative to pretreatment platelet aggregation, is a therapeutic target to which therapy should be tailored.

Superior early and consistent inhibition was observed over 24 hours following the high loading dose. For this reason, all pharmacodynamic studies examining clopidogrel loading strategies in stenting should include serial analyses over at least an 18-24 hour time period. There have been no previous pharmacodynamic investigations examining the effects of high clopidogrel loading doses with eptifibatide. This study suggests that 600 mg clopidogrel may also add to the anti-platelet effect of eptifibatide at 18-24 hours, as supported by observation of lower aggregation following stimulation with a high concentration of agonist. The definition of large infarcts in the present study has correlated with mortality in previous investigations (Saucedo et al. J Am Coll Cardiol. 2000; 35:1134-41; Ellis et al. Circulation. 2002; 106:1205-10; Brener et al. J Am Coll Cardiol. 2002; 40:1961-7).

Example 3

Platelet Reactivity and Clot Strength are Risk Factors for the Development of Ischemic Events within 6 Months This example examines the association of platelet reactivity and rapid thrombin generation upon the incidence of long-term ischemic events following coronary stenting. The following methods and materials were used in this example.

Patients.

This study was approved by the Investigational Review Board at Sinai Hospital of Baltimore. Consecutive patients undergoing non-emergent coronary stenting provided informed consent prior to the procedure. In order to be included in the study patients had to undergo successful percutaneous revascularization and be discharged from the hospital. Patients who gave informed consent but received coronary bypass surgery for revascularization were excluded. All patients were over 18 years old. Other exclusion criteria were: a history of bleeding diathesis, acute myocardial infarction within 48 hours, elevated cardiac markers (above upper limits normal for the respective assay), cerebrovascular event within 3 months, chronic vessel occlusion or angiographically visible thrombus, illicit drug or alcohol abuse, prothrombin time greater than 1.5 times control, platelet count <100,000/mm$^3$, hematocrit <30%, creatinine >4.0 mg/dl, and glycoprotein (GP) IIb/IIIa use prior to the procedure.

One hundred thirty-five patients received a loading dose of clopidogrel [300 mg (n=75), 600 mg (n=60)] in the catheterization laboratory immediately after successful stenting. Patients on a maintenance dose of clopidogrel at the time of admission (n=57) did not receive a loading dose. A GP IIb/IIIa inhibitor (n=92, all patients received eptifibatide) was administered at the discretion of the treating physician. Unfractionated heparin was administered according to the ESPRIT dosing regimen (60 U/kg) as a bolus to all patients receiving GP IIb/IIIa inhibitors and was dosed to achieve an activated clotting time of 300 seconds in those not treated with GP IIb/IIIa inhibitors (REF). All patients had received at least 81 mg aspirin for 7 days prior to the procedure and 325 mg was administered on the day of the procedure and daily thereafter. The maintenance dose of clopidogrel was 75 mg daily.

Blood Sampling.

Pretreatment blood samples were obtained in the catheterization laboratory before GP IIb/IIIa inhibitors or heparin administration through the indwelling femoral vessel sheath and transferred to vacutainer blood collecting tubes (Becton—Dickinson, Franklin Lakes, N.J.) containing 3.8. % trisodium citrate (for LTA Assay) or 40 USP lithium heparin (for thromboelastography platelet mapping assay) after discarding the first 2-3 ml of free flowing blood. The vacutainer tube was filled to capacity and gently inverted 3 to 5 times to ensure complete mixing of the anticoagulant. In those patients treated with GP IIb/IIIa inhibitors discharge blood samples were obtained at least 18 hours after cessation of therapy. In the remaining patients the discharge blood samples were obtained 24 hours post-procedure.

Light Transmittance Aggregometry (LTA).

Platelet aggregation was assessed as described previously (Matetzky et al. Circulation. 2004; 109:3171-5). Briefly, the blood-citrate tubes were centrifuged at 120 g for 5 minutes to recover platelet rich plasma (PRP) and further centrifuged at 850 g for 10 minutes to recover platelet poor plasma (PPP). The PRP and PPP were stored at room temperature to be used within two hours. Platelets were stimulated with 20 μM ADP and the aggregation was assessed using a Chronolog Lumi-Aggregometer (Model 490-4D) with the aggrolink software package (Chronolog, Havertown, Pa.). Aggregation was expressed as the maximum percent change in light transmittance from baseline, using PPP as a reference.

Thrombelastography Assay—Clot Strength, Thrombin Generation Time and ADP Induced Aggregation.

The TEG Hemostasis Analyzer 5000 Series with automated analytical software provides quantitative and qualitative measurements of the physical properties of a clot (Samara et al. Thromb Res. 2005; 115(1-2):89-94). In the present study, the maximum amplitude (MA) and the reaction time (R) were measured for the thrombin generated clot sample. MA is an indicator of the viscoelasticity of clot formation or clot strength and is dependent on platelet aggregation and fibrin formation and polymerization. R is the period of time of latency until initial fibrin formation and has been correlated with the velocity of thrombin generation (Rivard et al. Evaluation of the profile of thrombin generation during the process of whole blood clotting as assessed by thromboelastography. (AHA 2004, Abstract)).

One mL heparinized blood was transferred to a vial containing kaolin and mixed by inversion. Five hundred microliters of the activated blood was then transferred to a vial containing heparinase and mixed to neutralize heparin. The neutralized blood (360 μL) was added to a heparinase coated cup and assayed in the thromboelastography according to the manufacturer's instructions to obtain the thrombin-induced clot ($MA_{KH}$). The thromboelastography analytical software generated the MA as well as R values.

Heparinized blood (360 μL) was added to a non-coated cup containing reptilase and factor XIIIa activator to generate a whole blood crosslinked clot in the absence of thrombin generation ($MA_0$). A third sample (360 μL) of heparinized blood was added to a plain cup in the presence of the reptilase/XIIIa activator and ADP (2 μM) to generate whole blood-crosslinked clot with platelet activation ($MA_{ADP}$). Platelet inhibition in response to ADP was calculated using computerized software {according to manufacturer's instructions based on the formula: {% Inhibition=[(MAADP−MA0)/(MAKH−MA0)]×100.} and Percent aggregation (% MAADP) was determined by subtracting the % MAADP value from 100.

Clinical Outcomes.

Patients were contacted by telephone at the end of 1 month and six months to determine the occurrence of adverse events. Ischemic events were defined as the occurrence of death secondary to cardiovascular cause, myocardial infarction, stroke, stent thrombosis and recurrent ischemia diagnosed by the treating physician that required rehospitalization. Patients were divided into 2 groups based on the occurrence of adverse ischemic events.

Statistical Analysis.

Comparisons were made between the ischemic and non-ischemic groups by one way analysis of variance (Statistica software, Tulsa, Okla.). Based on the normal distribution of data the mean±SD is reported except as otherwise noted and p<0.05 was considered significant. A multivariate analysis was performed to determine risk factors for ischemic events.

Results

Patients and Clinical Outcomes

One hundred and ninety-two patients underwent catheter-based treatment and were analyzed. All of the procedures performed were non-emergent. Thirty six patients were admitted with unstable angina, and 11 patients had non-ST elevation myocardial infarction. The remainder of the patients had stable angina. The demographics and angiographic data of the patients with and without ischemic events are shown in Tables 7 and 8, respectively.

TABLE 7

Patient Demographics

|  | Patients with Ischemic Events (n = 38) | Patients without Ischemic Events (n = 154) | p-Value |
|---|---|---|---|
| Age (years) | 59 ± 10 | 62 ± 12 | NS |
| Race (Caucasian) n, (%) | 68 | 57 | NS |
| Gender (Male) n, (%) | 42 | 60 | 0.05 |
| BMI | 31 ± 7 | 30 ± 7 | NS |
| Risk Factors/Past medical Hx (%) | | | |
| Smoking | 39 | 45 | NS |
| Family history of CAD | 47 | 32 | NS |
| Hypertension | 81 | 63 | 0.04 |
| Hyperlipidemia | 92 | 57 | 0.001 |
| Diabetes | 50 | 40 | NS |
| Prior Myocardial Infarction | 24 | 40 | NS |
| Prior CABG | 18 | 26 | NS |
| Prior PTCA | | | |
| Pretreatment Medications (%) | | | |
| Beta blockers | 90 | 81 | NS |
| ACE Inhibitors | 74 | 61 | NS |
| Calcium blockers | 21 | 22 | NS |
| Lipid lowering agents | | | |
| 3A4 Pathway metabolized | 74 | 61 | NS |
| Non 3A4 Pathway metabolized | 18 | 24 | NS |
| Laboratory Data | | | |
| WBC (×1000/mm³) | 7.3 ± 2.3 | 7.6 ± 2.4 | NS |
| Platelets (×1000/mm³) | 244 ± 79 | 222 ± 66 | NS |
| Hemoglobin (g/dl) | 12.7 ± 2.3 | 13.3 ± 1.8 | NS |
| Creatinine (g/dl) | 1.1 ± 0.6 | 1.1 ± 1.8 | NS |

Data Reported as Mean ± SD;
ACE = angiotensin converting enzyme;
BMI = body mass index;
CABG = coronary artery bypass graft surgery;
CAD = coronary artery disease;
PTCA = percutaneous coronary angioplasty;
WBC = white blood cells;
3A4 = hepatic cytochrome 3A4

TABLE 8

Procedural Characteristics

|  | Patients With Ischemic Events (n = 38) | Patients Without Ischemic Events (n = 154) | p-Value |
|---|---|---|---|
| Length of procedure (min.) | 55.4 ± 22.3 | 62.1 ± 33.5 | NS |
| Ejection Fraction (%) | 47.5 ± 8.5 | 51.5 ± 9.0 | NS |
| Number of vessels treated | 1.25 ± 0.5 | 1.32 ± 0.6 | NS |
| Lesion Morphology | | | |
| Denovo (%) | 87 | 89 | NS |
| Culprit Lesion Location (%) | | | |
| LAD | 40 | 38 | NS |
| CX | 21 | 25 | NS |
| RCA | 34 | 30 | NS |
| SVG | 5 | 7 | NS |
| Stent Types (%) | | | |
| Drug eluting | 75 | 68 | NS |
| Bare metal | 18 | 29 | NS |
| PTCA only | 7 | 3 | NS |
| Reference vessel diameter (mm) | 3.0 ± 0.4 | 3.0 ± 0.5 | NS |
| Total lesion length (mm) | 21.9 ± 10.1 | 19.0 ± 12.2 | NS |
| Pre-stenosis (%) | 86 | 84 | NS |
| Post-stenosis (%) | 5 | 5 | NS |
| Procedural success (%) | 95 | 96 | NS |

Data Reported as Mean ± SD;
CX = circumflex artery;
LAD = left anterior descending artery;
RCA = right coronary artery;
SVG = saphenous vein graft There were more male patients without ischemia. Hypertension and hyperlipidemia were more common in patients with ischemia. There were no differences in medications between the two groups. Multivessel interventions were commonly performed and drug-eluting stents were often used. There were 4 in-hospital ischemic events. All of these patients had myocardial infarction. One of these patients had stent thrombosis.

Figure 13:
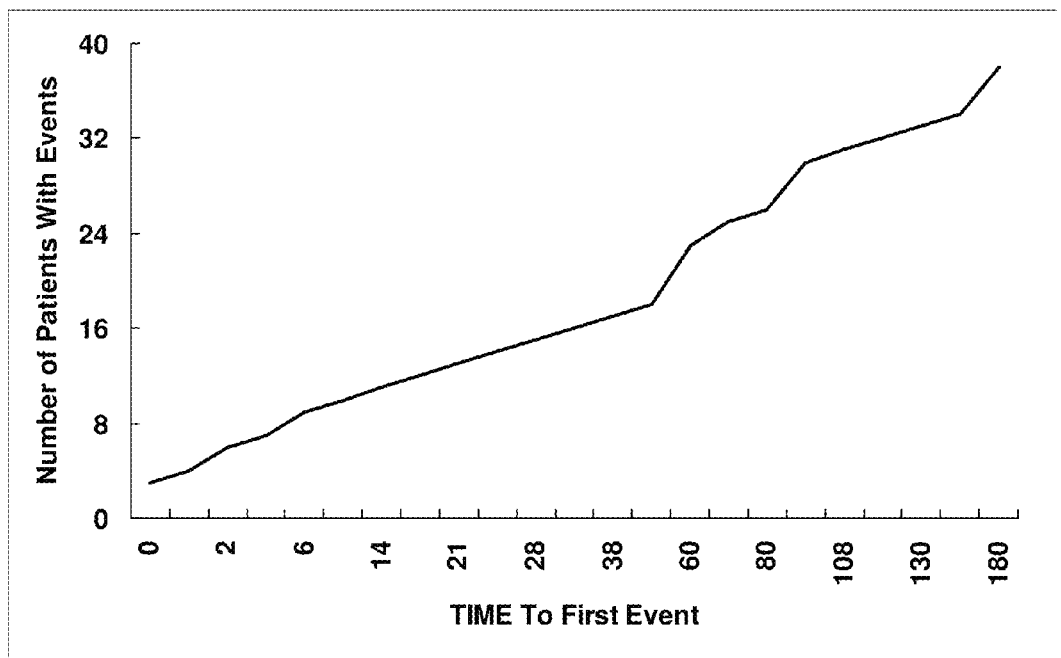
FIG. 13 is a graph demonstrating onset of first ischemic event.

Six month follow-up data were complete in 191/192 patients. There were 44 events that occurred in 38 patients (20%) within 6 months of discharge (FIG. 13). All events occurred during aspirin therapy. Thirty-two patients were receiving dual antiplatelet therapy at the time of their first event (about 17% treatment failure rate). Six patients had 2 events.

At one month post-discharge 20 of 191 patients (about 10%) had events. These events were: myocardial infarction (n=2), ischemia requiring revascularization of the prior target vessel (TVR) (n=2 patients), ischemia involving a vessel other than the prior target vessel requiring revascularization (non-TVR) (n=6), ischemia requiring hospitalization but not revascularization (n=9), and stroke (n=1). At 1-6 months 18 patients had the first occurrence of an event. These events were: death (n=2), ischemia requiring TVR (n=6), ischemia requiring non-TVR (n=4), ischemia requiring hospitalization but not revascularization (n=6). Six patients had the occurrence of a second event at 1-6 months. These events were: coronary artery bypass grafting (n=2), ischemia requiring TVR (n=1), ischemia requiring non-TVR (n=1), and ischemia requiring hospitalization but not revascularization (n=2).

Platelet Function Studies

One hundred-sixty patients had platelet aggregation measured by LTA and 192 samples were analyzed by thromboelastography (Table 9). Pretreatment aggregation by LTA was 73±9% in patients with ischemic events and 74±10 in patients without ischemic events (p=NS). There was no significant difference in platelet aggregation measured by thromboelastography (p=NS).

TABLE 9

Evaluation of Platelet Function Tests by Light Transmittance Aggregometry and Thrombelastography

|  | Patients With Ischemic Events | Patients Without Ischemic Events | p-Value |
|---|---|---|---|
| 20 µM ADP-Induced Pre-treatment Aggregation (%) | 73 ± 9 | 74 ± 10 | NS |
| 20 µM ADP-Induced Post-treatment Aggregation (%) | 63 ± 12 | 56 ± 16 | 0.02 |
| THROMBOELASTOGRAPHY % $MA_{ADP}$ Pre-treatment | 76 ± 14 | 71 ± 20 | NS |
| THROMBOELASTOGRAPHY % $MA_{ADP}$ Post-treatment | 59.3 ± 19 | 50 ± 20 | 0.02 |
| THROMBOELASTOGRAPHY MA (mm) | 73.9 ± 4.8 | 64.5 ± 4.0 | <0.001 |
| Reaction Time Pre-treatment (min) | 4.3 ± 1.3 | 4.6 ± 2.0 | NS |
| Reaction Time Post-treatment (min) | 4.3 ± 1.3 | 5.9 ± 1.5 | <0.001 |

Figure 14:
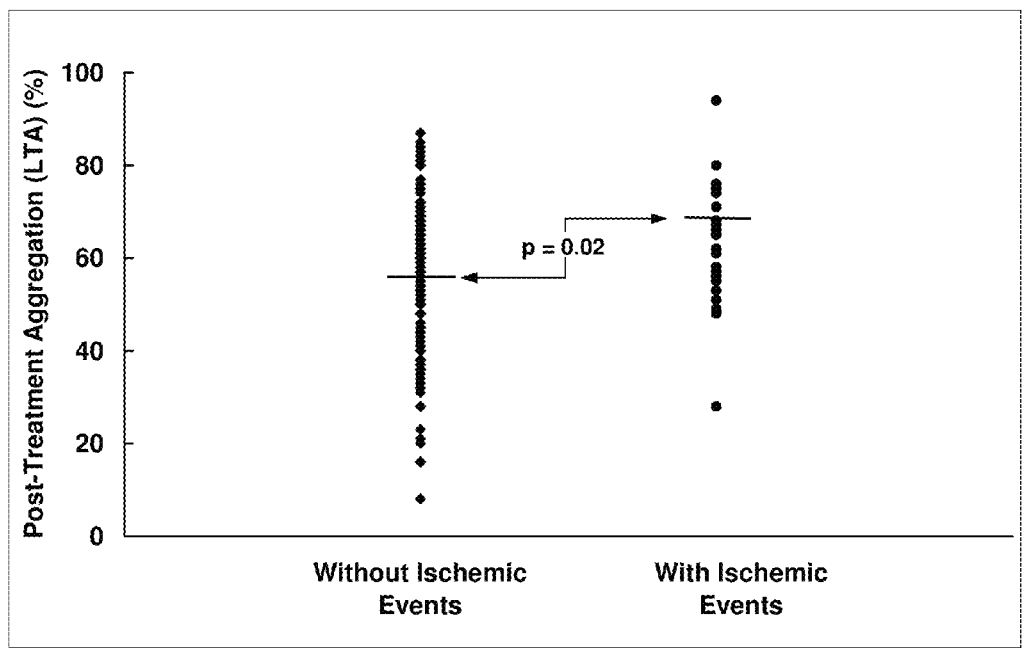
FIG. 14 is ADP induced post-treatment platelet aggregation (20 uM ADP) measured by light transmittance aggregometry (LTA) in patients without ischemic events and with ischemic events.
Figure 16:
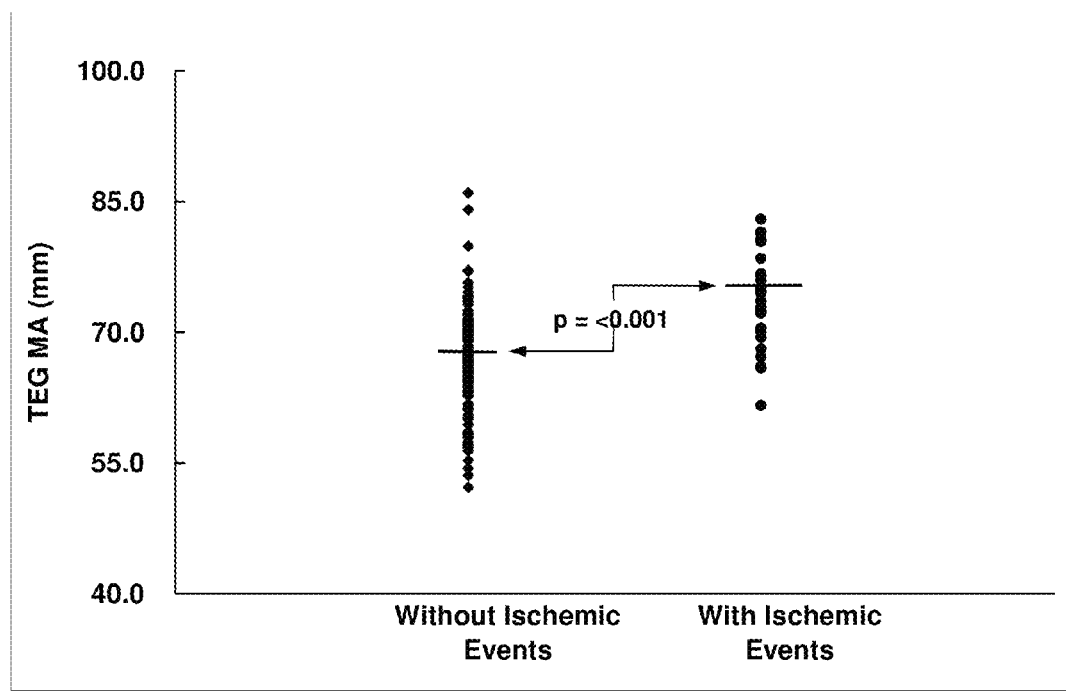
FIG. 16 is clot strength (MA) measured by thromboelastography in patients without ischemic events and with ischemic events.
Figure 18:
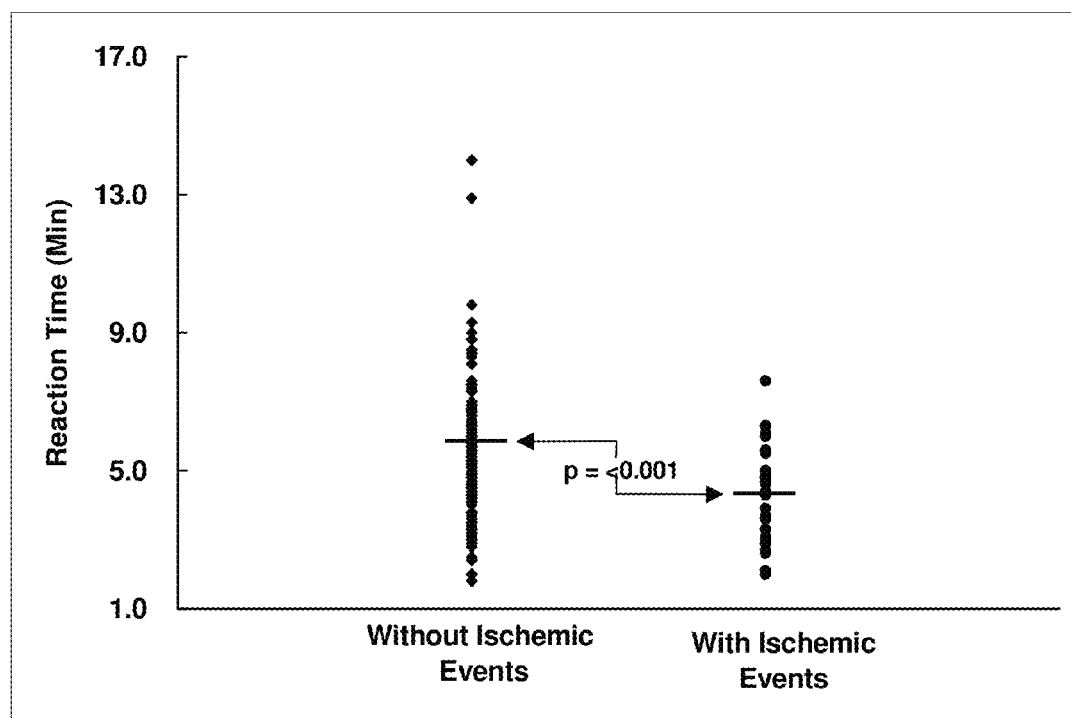
FIG. 18 is reaction time R measured by thromboelastography in patients with and without ischemic events.

Patients with ischemic events demonstrated a higher mean discharge platelet aggregation by LTA than patients without ischemic events (p=0.02, Table 9, FIGS. 14 and 15). Similarly, discharge platelet aggregation measured by thromboelstography was higher in patients with events than in patients without ischemic events (Table 9, p=0.02). Thomboelastography MA and thromboelastography R was also assessed in patient with and without ischemic events (FIGS. 18 and 19) The greatest frequency of patients with ischemic events was present in the highest quartiles of platelet reactivity measured by either LTA or thromboelastography measurement of maximum clot strength (MA) (FIGS. 16 and 17, respectively). Patients with ischemic events had significantly greater clot strength than patients without ischemic events p=<0.001 (FIG. 16). The reaction time R, was significantly shorter in patients with events (p=<0.001) (FIG. 18). Patients in the lowest two quartiles reaction time had the highest incidence of ischemic events (FIG. 19).

This example demonstrates that high ex-vivo platelet reactivity to ADP and (as well as) clot strength, and rapid thrombin generation measured at discharge are independent risk factors for the development of ischemic events within 6 months of elective coronary artery stenting. Since clot strength following stimulation with kaolin as measured by thromboelastography is dependent on platelet aggregation by thrombin, our findings strongly support the central role of platelet reactivity to both thrombin and ADP in atherothrombosis. All of these data indicate that the risk of in vivo platelet-related events can be assessed, in part, by ex vivo testing.

This example further demonstrates a near absence of ischemic events in patients with the lowest quartile of aggregation measured by LTA after ADP stimulation. However, since approximately 50% of events occurred in patients with average reactivity to ADP, an agonist other than ADP may be playing a dominant role in the genesis of ischemia. Moreover, 78% of patients suffering events had the highest clot strength measured by thromboelastography. Therefore maximum responsiveness to thrombin also appears to predict outcomes.

Thus, in those patients with average responsiveness to ADP, high reactivity to thrombin may be of central importance in ischemic event occurrence. This may be an explanation for ischemic events occurring in patients despite inhibition of ADP-induced aggregation by clopidogrel. Finally, these data indicate that the velocity of thrombin generation is also an independent risk factor that may be particularly relevant in patients with vigorous platelet aggregation in response to thrombin.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating a vascular disease in a patient, the method comprising:
   administering a treatment regimen comprising administration of an anti-platelet inhibitor to a patient having vascular disease; and
   administering an adjusted treatment regimen based on the risk of a thrombotic event in the patient,
   wherein the patient is at risk of a thrombotic event when a test score for the patient is greater than a risk threshold score based on a population study, wherein the test score is determined by assaying in vitro platelet function in a blood sample from the patient, wherein platelet function is assayed by assaying platelet reactivity, time-to-thrombin formation (TTF), or time-to-fibrin formation (TFF) in the blood sample in response to an agonist, and wherein assaying platelet reactivity is by a method other than assaying GP IIb/IIIa receptor expression, said assaying platelet function providing the test score, wherein the test score is independent of a pre-treatment baseline of platelet reactivity in the patient based on said identifying.

2. The method of claim 1, wherein the risk of a thrombotic event is risk of a thrombotic event within about 4 months to 12 months.

3. The method of claim 1, wherein the risk of a thrombotic event is risk of a thrombotic event within about 6 months to 12 months.

4. The method of claim 1, wherein the anti-platelet inhibitor is an anti-thrombotic agent selected from the group consisting of clopidogrel, enoxaparin, hirudin, hirulog and argatroban.

5. The method of claim 1, wherein the method comprises adjusting the treatment regimen to reduce platelet reactivity in the patient.

6. The method of claim 1, wherein at least one of TTF or TFF is assayed.

7. The method of claim 6, wherein TTF and TFF are assayed by thromboelastography R and the risk threshold score is from about 4.6 min to 5.6 min.

8. The method of claim 1, wherein the thrombotic event is a thrombosis.

9. The method of claim 8, wherein the thrombosis is a stent thrombosis.

10. The method of claim 1, wherein platelet reactivity is assayed by 20 µM ADP-induced platelet aggregation and the risk threshold score is from about 40% to 60% aggregation.

11. The method of claim 1, wherein platelet reactivity is assayed by a $P2Y_{12}$ reactivity ratio and the risk threshold score is from about 32 to about 48.

12. The method of claim 1, wherein platelet reactivity is assayed by a method other than thromboelastography maximum amplitude (MA).

13. The method of claim 1, wherein the risk of a thrombotic event is an immediate risk of a thrombotic event.

14. The method of claim 13, wherein platelet reactivity is assayed by 5 µM ADP-induced platelet aggregation or by 20 µM ADP-induced platelet aggregation.

15. The method of claim 14, wherein platelet reactivity is assayed by 5 µM ADP-induced platelet aggregation and the risk threshold score is from about 45% to 55% aggregation.

16. The method of claim 14, wherein platelet reactivity is assayed by 20 µM ADP-induced platelet aggregation and the risk threshold score is from about 52% to 76% aggregation.

17. The method of claim 13, wherein platelet reactivity is assayed by thromboelastography Maximum Amplitude (MA) and the risk threshold score is from about 58 mm to 86 mm.

18. The method of claim 13, wherein at least one of TTF or TFF is assayed.

19. The method of claim 18, wherein TTF and TFF are assayed by thromboelastography R and the risk threshold score is from about 4.6 min to 5.6 min.

20. The method of claim 1, wherein the immediate risk of a thrombotic event is risk of a thrombotic event within about 18 months.

21. The method of claim 1, wherein the immediate risk of a thrombotic event is risk of a thrombotic event within about 6 months.

22. The method of claim 1, wherein the thrombotic event is a recurrent thrombotic event.

23. The method of claim 1, wherein the recurrent thrombotic event is myocardial ischemia.

24. The method of claim 1, wherein the thrombotic event is myocardial ischemia.

25. The method of claim 24, wherein the thrombotic event is myocardial infarction, unstable angina, stable angina, restenosis, stroke or deep vein thrombosis.

* * * * *